US012746152B2

(12) United States Patent
Rotenstreich

(10) Patent No.: US 12,746,152 B2
(45) Date of Patent: Sep. 29, 2026

(54) INJECTION DEVICE WITH BOTH LINEAR AND ROTARY INDEPENDENT MOTOR DRIVES

(71) Applicant: TEL HASHOMER MEDICAL RESEARCH INFRASTRUCTURE AND SERVICES LTD., Ramat Gan (IL)

(72) Inventor: Ygal Rotenstreich, Ramat Gan (IL)

(73) Assignee: TEL HASHOMER MEDICAL RESEARCH INFRASTRUCTURE AND SERVICE LTD., Ramat Gan (IL)

( * ) Notice: Subject to any disclaimer, the term of this patent is extended or adjusted under 35 U.S.C. 154(b) by 841 days.

(21) Appl. No.: 18/021,622

(22) PCT Filed: Aug. 17, 2021

(86) PCT No.: PCT/IB2021/057566
§ 371 (c)(1),
(2) Date: Feb. 16, 2023

(87) PCT Pub. No.: WO2022/038516
PCT Pub. Date: Feb. 24, 2022

(65) Prior Publication Data

US 2023/0301829 A1 Sep. 28, 2023

(30) Foreign Application Priority Data

Aug. 18, 2020 (IL) .......................................... 276795

(51) Int. Cl.
*A61F 9/00* (2006.01)
*A61F 9/007* (2006.01)
(Continued)

(52) U.S. Cl.
CPC ........ *A61F 9/0017* (2013.01); *A61F 9/00736* (2013.01); *A61M 5/20* (2013.01); *A61M 2005/206* (2013.01); *A61M 5/31* (2013.01)

(58) Field of Classification Search
CPC ... A61B 2017/3407; A61B 2017/3409; A61M 5/3287; A61M 5/329; A61M 2005/3289
See application file for complete search history.

(56) References Cited

U.S. PATENT DOCUMENTS 5,385,148 A 1/1995 Lesh et al.
5,397,323 A * 3/1995 Taylor .................... A61B 34/71 901/41

(Continued)

OTHER PUBLICATIONS

Chia A., et al., "Five-Year Clinical Trial on Atropine for the Treatment of Myopia 2: Myopia Control with Atropine 0.01% Eyedrops," Ophthalmology, Feb. 2016, vol. 123(2), pp. 391-399.

(Continued)

*Primary Examiner* — Laura A Bouchelle
(74) *Attorney, Agent, or Firm* — The Roy Gross Law Firm, LLC; Roy D. Gross

(57) ABSTRACT

Embodiments pertain to an apparatus for injecting a medicament into a tissue, the apparatus comprising: a rotary motion drive having a motion drive rotary axis and which is configured to receive a needle and operable to rotate the needle about the motion drive rotary axis; and a linear motion drive comprising a drive screw and configured to translate the needle selectively in either proximal and distal direction along a translation axis, and further configured such that, when the apparatus is operably engaged with the tissue, the drive screw remains translationally stationary relative to the tissue during operation of the rotation motion drive to longitudinally translate the needle; and wherein the rotary motion drive and the linear motion drive are independently operatable.

20 Claims, 9 Drawing Sheets

(51) Int. Cl.
*A61M 5/20* (2006.01)
*A61M 5/31* (2006.01)

(56) References Cited

U.S. PATENT DOCUMENTS

| | | | | |
|---|---|---|---|---|
| 5,649,956 | A * | 7/1997 | Jensen | B25J 18/04 606/1 |
| 6,193,673 | B1 | 2/2001 | Viola et al. | |
| 6,554,779 | B2 | 4/2003 | Viola et al. | |
| 7,722,549 | B2 | 5/2010 | Nakao | |
| 7,954,778 | B2 * | 6/2011 | Osawa | A61F 9/007 248/278.1 |
| 8,968,212 | B2 | 3/2015 | Speeg et al. | |
| 10,449,302 | B2 | 10/2019 | Olson et al. | |
| 10,470,928 | B2 | 11/2019 | Horvath et al. | |
| 10,632,281 | B2 | 4/2020 | Rosenman et al. | |
| 2004/0158173 | A1 | 8/2004 | Voegele et al. | |
| 2012/0016311 | A1 | 1/2012 | Altman et al. | |
| 2013/0172909 | A1 | 7/2013 | Harris | |
| 2016/0074217 | A1 | 3/2016 | Price et al. | |
| 2016/0287438 | A1 | 10/2016 | Badawi et al. | |
| 2020/0338277 | A1 | 10/2020 | Franke et al. | |

OTHER PUBLICATIONS

Curtin B.J., et al., "Axial Length Measurements and Fundus Changes of the Myopic Eye," American Journal of Ophthalmology, Jan. 1971, vol. 71(1 Pt 1), pp. 42-53.
Dayan Y.B., et al., "The Changing Prevalence of Myopia in Young Adults: A 13-year Series of Population-based Prevalence Surveys," Investigative Ophthalmology & Visual Science, Aug. 2005, vol. 46(8), pp. 2760-2765.
Farbrother J.E., et al., "Family Aggregation of High Myopia: Estimation of the Sibling Recurrence Risk Ratio," Investigative Ophthalmology Visual Science, Sep. 2004, vol. 45(9), pp. 2873-2878.
Gordon R.A., et al., "Refractive Development of the Human Eye," Archives of Ophthalmology, Jun. 1985, vol. 103 (6), pp. 785-789.
Guggenheim J.A., et al., "The Heritability of High Myopia: A Reanalysis of Goldschmidt's Data," Journal of Medical Genetics, Mar. 2000, vol. 37(3), pp. 227-231.
Guo Y., et al., "Myopic Shift and Outdoor Activity Among Primary School Children: One-year Follow-up Study in Beijing," PLoS One, Sep. 2013, vol. 8(9), pp. e75260.
He M., et al., "Prevalence of Myopia in Urban and Rural Children in Mainland China," Optometry and Vision Science, Jan. 2009, vol. 86(1), pp. 40-44.
International Search Report and Written Opinion for Application No. PCT/IB2021/057566, mailed Dec. 16, 2021, 19 pages.
Israel Office Action for Patent Application No. 276795 dated Apr. 14, 2021, 14 pages—English Translation Available.
Jones L.A. et al., "Comparison of Ocular Component Growth Curves Among Refractive Error Groups in Children," Investigative Ophthalmology Visual Science, Jul. 2005, vol. 46(7), pp. 2317-2327.
Kempen J.H., et al., "The Prevalence of Refractive Errors Among Adults in the United States, Western Europe, and Australia," Archives of Ophthalmology, Apr. 2004, vol. 122(4), pp. 495-505.
Kim E.C., et al., "Prevalence and risk factors for refractive errors: Korean National Health and Nutrition Examination Survey 2008-2011," PLoS One, Nov. 2013, vol. 8(11), pp. e80361.
Lin Z., et al., "Near Work, Outdoor Activity, and Their Association With Refractive Error," Optometry and Vision Science, Apr. 2014, vol. 91(4), pp. 376-382.
Morgan I., et al., "How Genetic Is School Myopia?," Progress in Retinal and Eye Research, Jan. 2005, vol. 24 (1), pp. 1-38.
Morgan I.G., et al., "Myopia," Lancet, May 2012, vol. 379(9827), pp. 1739-1748.
Mutti D.O., et al., "Parental Myopia, Near Work, School Achievement, and Children's Refractive Error," Investigative Ophthalmology Visual Science, Dec. 2002, vol. 43(12), pp. 3633-3640.
Naidoo K.S., et al., "Refractive Error and Visual Impairment in African Children in South Africa," Investigative Ophthalmology Visual Science, Sep. 2003, vol. 44(9), pp. 3764-3770.
Rose P.S. et al., "Stickler Syndrome: Clinical Characteristics and Diagnostic Criteria," American Journal of Medical Genetics. Part A, Oct. 2005, vol. 138A(3), pp. 199-207.
Saw S.M., et al., "Myopia and Associated Pathological Complications," Ophthalmic Physiological Optics, Sep. 2005, vol. 25(5), pp. 381-391.
Seet B., et al., "Myopia in Singapore: Taking a Public Health Approach," The British Journal of Ophthalmology, May 2001, vol. 85(5), pp. 521-526.
Shoko, T., et al., "National Survey Results of Pathological Myopia", Suda Department of Ophthalmology, Tokyo Medical and Dental University.
Song Y.Y., et al., "Atropine in Ameliorating the Progression of Myopia in Children With Mild to Moderate Myopia: A Meta-analysis of Controlled Clinical Trials," Journal of Ocular Pharmacology and Therapeutics, Aug. 2011, vol. 27 (4), pp. 361-368.
Tokoro T., et al., "Results of Investigation of Pathologic Myopia in Japan: Report of Myopic Chorioretinal Atrophy," Tokyo: Ministry of Health and Welfare, 1982, pp. 32-35.
Verhoeven V.J.M., "What Causes Myopia?," Erasmus MC: University Medical Center Rotterdam / Dissertation, Jun. 16, 2015, 273 pages. Retrieved from [ http://hdl.handle.net/1765/78245].
Vitale S., et al., "Increased Prevalence of Myopia in the United States Between 1971-1972 and 1999-2004," Archives of Ophthalmology, Dec. 2009, vol. 127(12), pp. 1632-1639.
Vongphanit J., et al., "Prevalence and Progression of Myopic Retinopathy in an Older Population," Ophthalmology, Apr. 2002, vol. 109(4), pp. 704-711.
Williams K. M., et al., "Increasing Prevalence of Myopia in Europe and the Impact of Education," Ophthalmology, Jul. 2015, vol. 122(7), pp. 1489-1497.
Wojciechowski R., "Nature and Nurture: The Complex Genetics of Myopia and Refractive Error," Clinical Genetics, Apr. 2011, vol. 79(4), pp. 301-320.
Wolfram C., et al., "Prevalence of Refractive Errors in the European Adult Population: The Gutenberg Health Study (GHS)," The British journal of ophthalmology, Jul. 2014, vol. 98(7), pp. 857-861.
Extended European Search Report for European Application No. 21857870.6, mailed Jul. 30, 2024, 08 Pages.

* cited by examiner

FIG. 4A FIG. 4B FIG. 4C
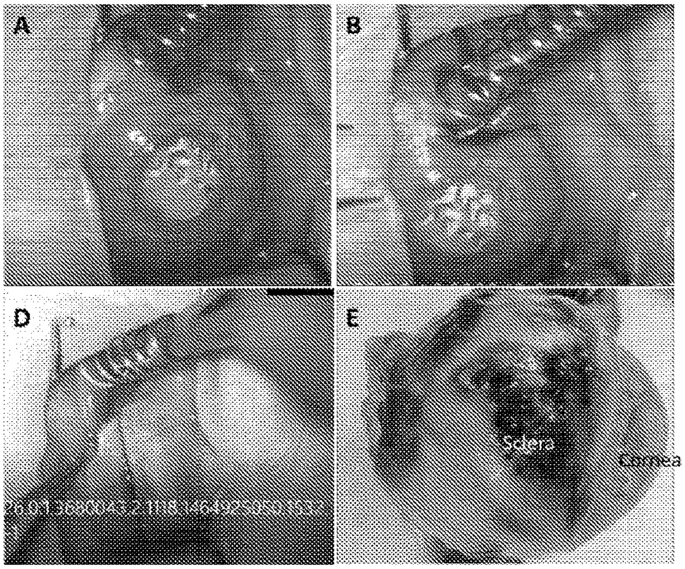
FIG. 4D FIG. 4E
FIG. 5
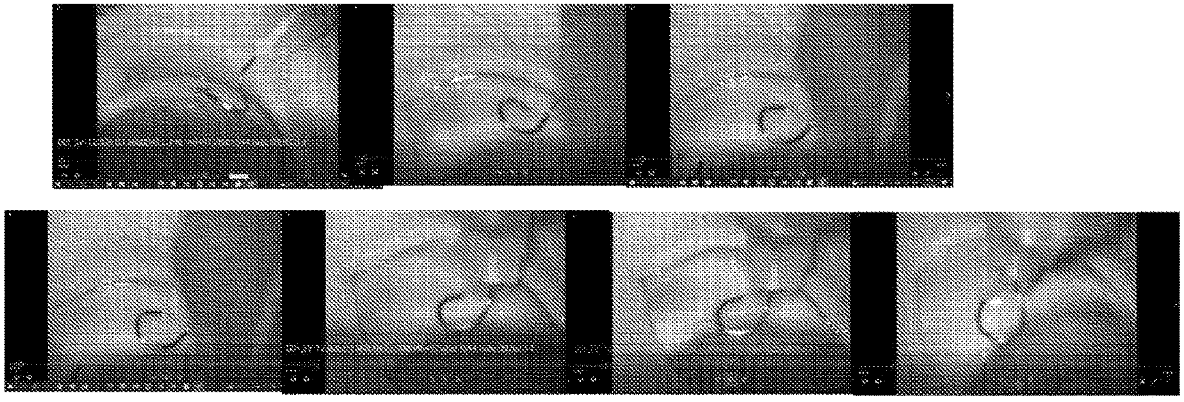

INJECTION DEVICE WITH BOTH LINEAR AND ROTARY INDEPENDENT MOTOR DRIVES

CROSS-REFERENCE TO RELATED APPLICATIONS

This patent application is a National Phase of PCT Patent Application No. PCT/IB2021/057566 having International filing date of Aug. 17, 2021, which claims the priority of Israel Patent Application 276795, filed Aug. 18, 2020, which are all incorporated herein by reference in their entirety.

FIELD

Embodiments of the disclosure relate to apparatus and methods for delivering a medicament to a biological tissue region.

BACKGROUND

Delivery of medicaments for treatment of a medical condition is often a complex procedure that may be difficult to carry out with a desired degree of spatial and temporal resolution. For example, myopia (short sightedness) is a common refractive state of the eye that is usually caused by elongation of the eyeball. High myopia, defined as requiring correction of more than −6 diopters, is associated with a significant risk of developing visual complications, including myopic macular degeneration, glaucoma, and retinal detachment, and is associated with increased risk for visual loss. It is estimated that in the next ten years about 2.5 billion people worldwide will have myopia, more than 10% of these people (375 million) will have high myopia, and that 49 million will develop severe visual impairment as a result of this condition.

The currently accepted hypothesis of myopia development is that excessive eye growth generated by signals produced by the retina affect the overlying sclera and cause elongation of the eyeball. Treatment to prevent or slow elongation of the eyeball and development of associated myopia may involve introducing into the sclera a medicament to promote scleral crosslinking that mechanically stiffens the sclera and thereby operates to moderate elongation of the eye. The medicament may be a photosensitizer, such as UVA (ultraviolet A radiation) activated riboflavin (RF), which requires delivery of a sufficient amount of the photosensitizer into the sclera and subsequent illumination of the delivered photosensitizer with UVA light, without causing radiation damage to surrounding tissue.

BRIEF DESCRIPTION OF THE FIGURES

Non-limiting examples of embodiments of the invention are described below with reference to figures attached hereto that are listed following this paragraph. Identical features that appear in more than one figure are generally labeled with a same label in all the figures in which they appear. A label labeling an icon representing a given feature of an embodiment of the invention in a figure may be used to reference the given feature. Dimensions of features shown in the figures are chosen for convenience and clarity of presentation and are not necessarily shown to scale.

FIGS. 4A-4E are photographs depicting injection of a dye (indocyanine green) into the sclera and detection thereof. The dye was injected 3 mm from the limbus in live rabbit eyes, using a NeedleTwist device described herein. A coiled piercer was spun in a helical movement creating a superficial scleral pocket (FIGS. 4B-D). The dye was detected in the back of the eye area (FIG. 4E).

FIG. 5 are photographs demonstrating stages of injection of riboflavin A to eyes of live rabbits, using a NeedleTwist device.

DETAILED DESCRIPTION

Figure 1A:
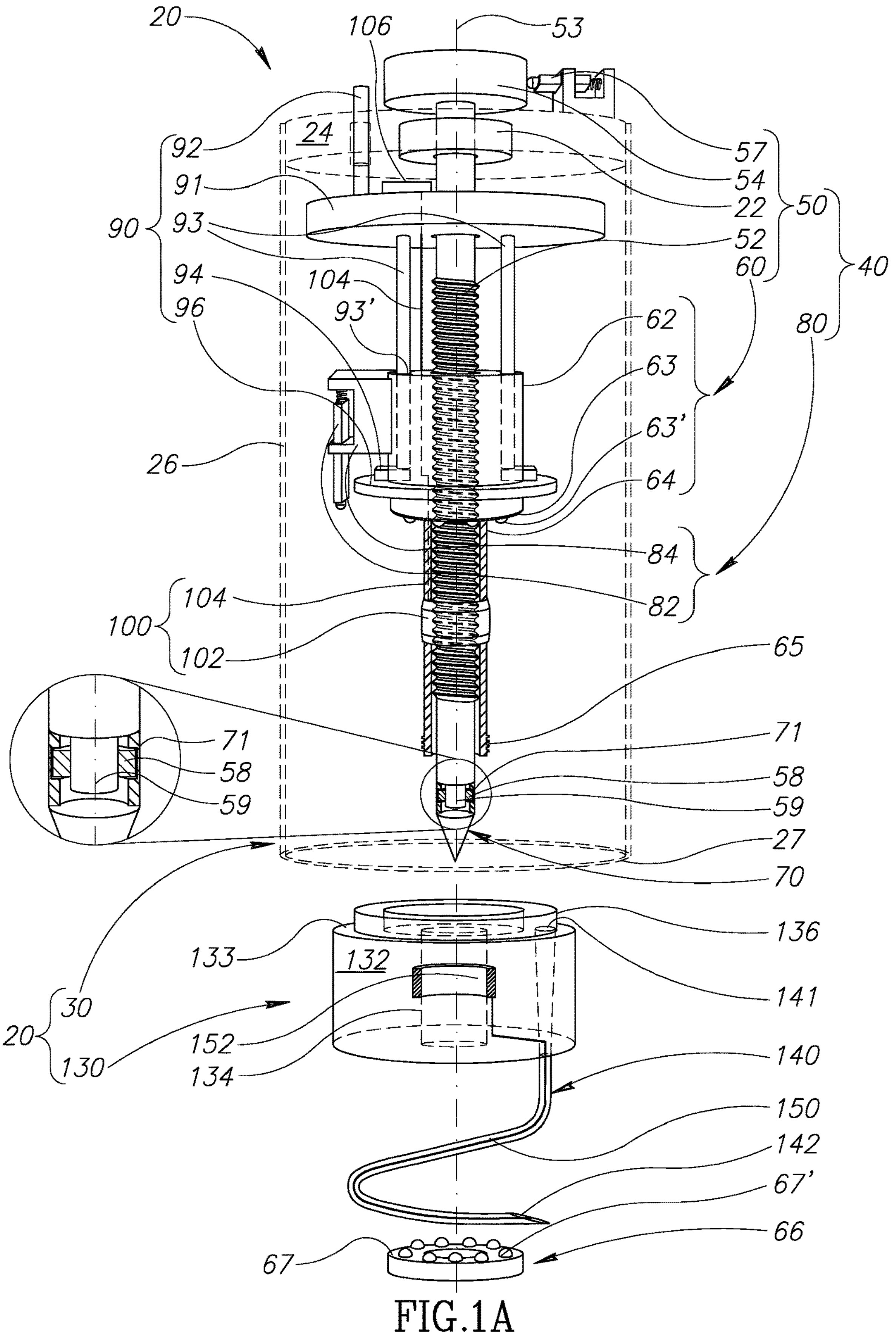
FIG. 1A schematically shows a partially exploded view of a NeedleTwist medicament delivery apparatus comprising a deployer and a disposable needle cartridge for mounting to the deployer, in accordance with an embodiment of the disclosure.
Figure 1B:
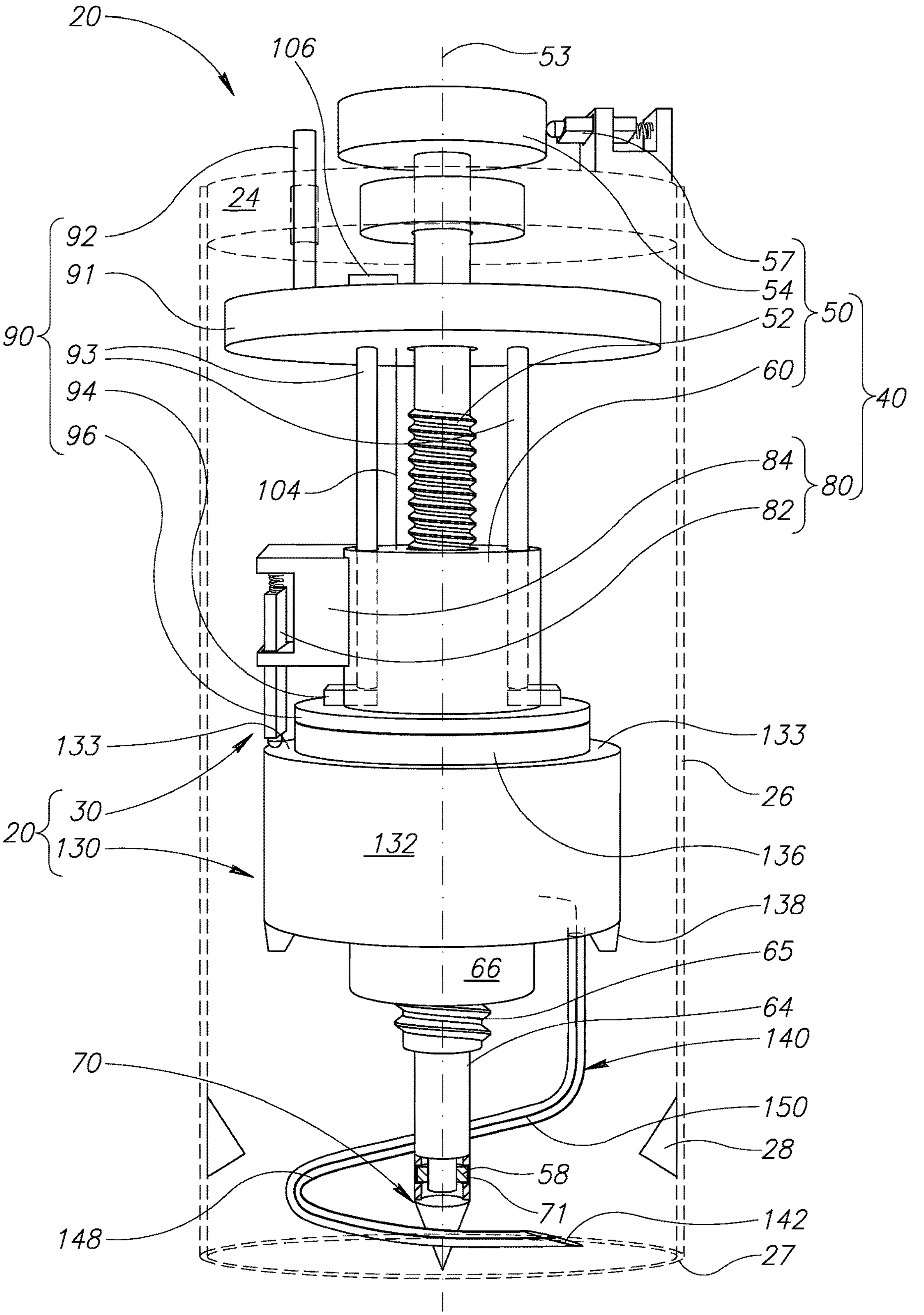
FIG. 1B schematically shows the NeedleTwist shown in FIG. 1A with the disposable needle cartridge mounted to the deployer, in accordance with an embodiment of the disclosure.

FIGS. 1A and 1B schematically show a NeedleTwist 20 comprising a NeedleTwist receiver 30 and an (e.g., disposable) NeedleTwist needle cartridge 130 configured to be mounted to and operated by the receiver to deliver a desired dose of a medicament to a tissue region. The needle cartridge 130 may thereafter be dismounted, e.g., for disposal, in accordance with an embodiment of the disclosure.

FIG. 1A schematically shows NeedleTwist 20 prior to mounting needle cartridge 130 to receiver 30. FIG. 1B schematically shows NeedleTwist 20 assembled with needle cartridge 130 mounted to receiver 30.

Receiver 30 optionally has a deployer 40 comprising a linear motion screw drive 50 for axial displacement of a needle 140, and a rotary motion drive 80 for rotation of a needle 140.

Linear motion screw drive 50 comprises a drive screw 52 having an axis 53, and a drive stage 60 for linear displacement of the needle.

In some examples, needle 140 may be a straight needle having a straight longitudinal needle axis. In some examples, when coupled with the device's cartridge, the straight needle axis may be positioned off-axis (e.g., parallel or substantially parallel) relative to linear motion screw drive 50. In some other examples, needle 140 may be contorted and have, for example, a helical configuration defining a twist axis. In some configurations, the needle's twist axis may coincide with axis 53 of linear motion screw drive 50. In some other configurations, the needle's twist axis may be off-axis relative to axis 53 of linear motion screw drive 50.

NeedleTwist 20 may be configured such that when operably engaged with a tissue region, the drive screw 52 remains axially stationary (i.e., it does not translate relative to the tissue region), during rotation thereof for axially displacing needle 140 in proximal direction towards the tissue region, or in distal direction away from the tissue region.

For example, drive screw 52, which may be formed having a disc shaped transmission head 54, may be held by a bearing 22 mounted to a deployer support plate 24 of a NeedleTwist housing 26. In some examples, the deployer support plate 24 is movable in the housing longitudinally parallel to axis 53.

In some embodiments, linear motion screw drive 50 may be operably coupled with NeedleTwist housing 26 such that when NeedleTwist housing 26 is operably engaged with and held in place against a surface (e.g., a tissue region), drive screw 52 remains axially stationary when being rotated, i.e., it does not translate relative to the tissue region or NeedleTwist housing 26. As a result, rotation of drive screw 52 causes linear displacement of drive stage 60 relative to the surface.

NeedleTwist housing 26 may have a bottom edge 27 configured for operably engaging with tissue. Bottom edge 27 may be shaped to facilitate delivery of medicament to the tissue region. For example, edge 27 may be angled and shaped to advantageously engage with tissue without damaging the tissue. For use in delivering medicament to a patient's eye, edge 27 may be shaped to conform or fit the curvature of the eyeball or other tissue, e.g., for engaging with tissue without damaging it. In some examples, bottom edge 27 may include a soft layer (not shown), e.g., for engaging with tissue without damaging it.

Drive stage 60 may have a main body 62 threaded onto the drive screw and a circularly cylindrical stem 64 on which needle cartridge 130 is mountable.

In some examples, a (e.g., piezoelectric) drive screw motor 57 may be coupled with drive screw 52. For example, drive screw motor 57 may be coupled transmission head 54 and is operable to rotate transmission head 54 and thereby drive screw 52 selectively clockwise or counterclockwise to translate drive stage 60 along axis 53 away from and "downwards" towards edge 27 (in proximal direction) or "upwards" away from edge 27, and toward the transmission head (in distal direction). In some other examples, transmission head 54 may be rotated manually.

Viewed along axis 53 from transmission head 54 end of drive screw 52, and assuming by way of example that the drive screw is left-hand threaded, clockwise rotation of transmission head 54 translates drive stage 60 along axis 53 away from the transmission head and downwards toward edge 27. Counterclockwise rotation of transmission head 54 translates drive stage 60 along axis 53 away from and upwards toward the transmission head.

Needle cartridge 130 may be rotatably coupled with drive stage 60 or with housing 26 such that the needle cartridge 130 can rotate relative to the axis of drive stage 60 or housing 26, while being (e.g., form-fittingly) secured to prevent axial displacement of needle cartridge 130 relative to drive stage 60 or housing 26.

In some embodiments, stem 64 may be configured to allow rotatable coupling of needle cartridge 130 with stem 64. In some examples, stem 64 and needle cartridge 130 may be configured such that once they are coupled with each other, needle cartridge 130 can rotate relative to stem 64, while being axially secured relative to stem 64. For instance, needle cartridge 130 may be form-fittingly coupled with stem 64 to prevent axial displacement of needle cartridge 130 relative to stem 64, while allowing rotation of needle cartridge 130 around the axis of stem 64.

In some examples, stem 64 may comprise an annular groove or recess (not shown) for receiving a corresponding snapring (not shown) of needle cartridge 130. In other configurations, stem 64 may comprise an annular shoulder configured to snap-fittingly receive a corresponding snapring. It is noted that alternative configurations, needle cartridge 130 may comprise an annular groove, and stem 64 may comprise a snapring. In yet further alternative configurations, needle cartridge 130 may comprise an annular shoulder and stem 64 may comprise a snapring such that needle cartridge 130 and stem 64 may be rotatably coupled with each other while being form-fittingly secured with each other with respect to axial displacement relative to each other.

In some other examples, stem 64 may be formed having a threaded end 65 onto which a mounting nut 66 may be screwed to secure needle cartridge 130 to stem 64, as shown in FIG. 1B and described below.

A top surface 67 of mounting nut 66 and a bottom surface 63 of main body 62 comprise bearings 67' and 63' respectively to enable rotation of needle cartridge 130 about axis 53 of drive screw 52 when needle cartridge 130 is secured to stem 64. Drive screw 52 optionally comprises a bearing 58 mounted to a distal end 59 of drive screw 52.

A disposable tissue contact anchor tip 70, shown partially cutaway, may be rotatably mounted to the drive screw, e.g., by pushing the anchor onto end 59 of the drive screw until the anchor snap catches the bearing in a receiving groove 71 of the anchor. This way, axial displacement of contact anchor tip 70 relative to drive screw 52 is prevented, while allowing rotation of anchor tip 70 about the drive screw axis 53.

Operation of tissue contact anchor tip 70 and variations of a tissue contact anchor in accordance with an embodiment of the disclosure are discussed below with reference to FIGS. 2A-2D and FIG. 3A.

Cartridge rotary drive 80 may comprise at least one (e.g., piezoelectric) cartridge motor 82 held by a support arm 84 that extends from main body 62 of drive stage 60. Cartridge motor 82 is operable to selectively rotate needle cartridge 130 clockwise or counterclockwise when the needle cartridge is mounted to stem 64. Operation of cartridge rotary drive 80 in rotating the needle cartridge is described below.

Syringe system 90 may comprise a syringe activation plate 91 having at least one alignment and syringe activation button 92 that extends through and protrudes out from deployer support plate 24.

Syringe activation plate 91 may be coupled with a plunger, piston or any other (e.g., depression) mechanism configured to impart pressure onto the medicament reservoir for the pressurized release of fluid (e.g., liquid, gas, or a liquid-gas mixture), from the reservoir via a needle that can be brought in fluid communication with the reservoir, into the tissue region. The depression mechanism may comprise an (e.g., rubber) foot such as, for example, a pressure annulus 96, which upon activation of the syringe activation plate 91, applies pressure onto the medicament reservoir, thereby causing release of the medicament via the needle.

In some examples, the depression mechanism may comprise a plurality of depression rods 93 that extend from the activation plate and into guide holes 93' formed in main body 62 of drive stage 60. Each depression rod 93 is connected to a mounting foot 94 that protrudes out from main body 62 through slots (not shown) formed in the main body and holds pressure annulus 96. Lengths and sizes of guide holes 93' and the slots are determined to enable motion of activation plate 91, and thereby pressure annulus 96, away from or towards deployer support plate 24.

In some examples, at least one activation and alignment button 92 prevents rotation of drive stage 60 about drive screw axis 53. This way, rotation of transmission head 54 forces linear translation of drive stage 60 relative to NeedleTwist housing 26.

Button 92 may be configured such that when activated (e.g., depressed) causes the depression of activation plate 91 to thereby push pressure annulus 96 away from deployer support plate 24.

As described below with reference to FIG. 1B, activating button 92 to depress activation plate 91 and thereby pressure annulus 96 away from deployer support plate 24 may be used to inject a quantity of medicament stored in needle cartridge 130 into a tissue region being treated using NeedleTwist 20.

Although embodiments of the NeedleTwist described herein are configured such that syringe system 90 is external relative to motion screw drive 50 such that drive screw 52 extends through a corresponding threaded bore of the drive stage 60, this should by no means be construed in a limiting manner. Accordingly, in some other embodiments, the NeedleTwist may be configured such that, for example, a needle cartridge can be disposed internally and, e.g., concentrically arranged relative to an outer hollow drive screw having an internal thread. The internal thread of the hollow drive screw may operably cooperate with an outer thread of the internal drive stage. The medicament may be disposed in the internal drive stage. Correspondingly, a syringe system may be configured to have, for example, a disc-shaped, pressure plate for imparting pressure onto the internal medicament reservoir.

In an embodiment, NeedleTwist 20 comprises an energy applicator such as, for example, a radiation delivery system 100. The energy applicator is operable to provide needle cartridge 130 with radiation advantageous for subjecting a region, into which needle cartridge is operated to deliver a medicament, with (e.g., electromagnetic and/or radioactive) radiation.

Radiation delivery system 100 may comprise at least one, optionally annular shaped radiation source (e.g., light source) 102, mounted, for example, to stem 64 of drive stage 60. Radiation source 102 may be connected via electrical conductors 104 to a power supply or power source 106 operable to excite the radiation source to radiate. In an embodiment, radiation source 102 is configured to radiate, infrared EM radiation, ultraviolet EM radiation such as, e.g., UVA light, blue light and/or EM radiation in additional or alternative wavelength ranges.

In some embodiments, disposable needle cartridge 130 comprises an annular needle cartridge housing 132 formed having a circular through hole indicated by a dashed cylinder 134 that is dimensioned to receive stem 64 of drive stage 60.

An optionally annular medicament reservoir 136, configured to receive or prefilled with a medicament (not shown) to be dispensed by NeedleTwist 20, is mounted to a top surface 133 of housing 132. In some examples, (e.g., annular) medicament reservoir 136 may include, for example, a compressible bag filled with a medicament, an elastic, and/or sponge-like material including (e.g., soaked with) a medicament. The medicament is to be dispensed by NeedleTwist 20. A hollow helical or otherwise contorted needle 140 that may be coupled with reservoir 136 to be brought in fluid communication with a medicament via an orifice 141. For example, needle 140, which comprises a needle end 142, may be mounted to, e.g., housing 132.

In an embodiment, NeedleTwist 20 comprises at least one waveguide (e.g., optical fiber) configured to receive light by radiation source 102 to deliver the received light to illuminate tissue into which the needle is inserted. For example, the at least one optical fiber may be mounted to an outside surface of and/or inside the lumen of helical needle 140 to receive light provided by radiation source 102, e.g., when needle cartridge 130 is mounted to stem 64, and deliver the received light to illuminate tissue into which the needle is inserted, in accordance with an embodiment of the disclosure.

By way of example, FIG. 1A schematically shows an optical fiber 150 mounted inside the lumen of helical needle 140. The optical fiber exits the needle to optically contact an optionally annular optical coupler 152 mounted in through hole 134. Optical coupler 152 is configured to match and make optical contact with radiation source 102 and couple radiation provided by the radiation source into the optical fiber when needle cartridge 130 is mounted to stem 64 of drive stage 60.

Needle cartridge 130 may be mounted to NeedleTwist 20 by sliding housing 132 onto stem 64 so that a region of top surface 133 of the housing contacts bearings 63' of main body 62. In some examples, the needle cartridge may be secured in place by screwing mounting nut 66 onto threaded end of stem 64. When secured in place as schematically shown in FIG. 1B, (e.g., piezoelectric) needle cartridge housing 132 is rotatably sandwiched between bearings 67' of mounting nut 66 and bearings 63' of main body 62.

With cartridge 130 mounted to NeedleTwist 20, (e.g., piezoelectric) drive screw motor 57 is controllable to rotate transmission head 54 and thereby drive screw 52 to translate the mounted cartridge 130 downwards or upwards along axis 53 relative to edge 27 of housing 26.

Downward motion towards edge 27 moves the cartridge and helical needle 140 towards a region of tissue being operated on, to deliver medicament to the tissue region using NeedleTwist 20. Upward motion away from edge 27 moves the cartridge and helical needle 140 away from the tissue region.

Independent from drive screw motor 57, Piezoelectric motor 82 of rotary drive 80 is controllable to rotate cartridge 130 and thereby helical needle 140 about axis 53 and relative to the tissue region, independent of linear motion of cartridge 130 along axis 53 provided by linear motion screw drive 50.

Motion provided by linear motion screw drive 50 and rotary drive 80 may be controlled to puncture the tissue region and advantageously position end 142 of the needle inside the tissue region.

When helical needle 140 is advantageously positioned inside the tissue region, activation button 92 of syringe system 90 may be depressed to push pressure annulus 96 down onto, e.g., elastic, reservoir 136 to push medicament contained in the reservoir out from the reservoir through helical needle 140 and into the tissue region.

To position NeedleTwist 20 in preparation for using NeedleTwist to inject the medicament into the tissue region, housing 26 may be placed on or near to the tissue region so that edge 27 of the housing seats on or near to the tissue region. Once edge 27 is seated on or near the tissue region, deployer support plate 24 may be moved inside housing 26 along axis 53 to move anchor tip 70 to contact and optionally penetrate the tissue region. Contacting the tissue region with edge 27 and placing or puncturing the tissue region with anchor tip 70 operates to stabilize NeedleTwist 20 on tissue region and facilitate accurate control of movement and positioning of helical needle 140 relative to the tissue region.

In an embodiment of the disclosure, housing 26 may be held by a support (e.g., robotic) arm (not shown) which may operate automatically and/or be at least partially manually operated to position NeedleTwist 20 onto a tissue region into which NeedleTwist is used to inject a medicament. Optionally, the support arm is automatically and/or at least partially manually operable to position housing 26 so that edge 27 of the housing seats advantageously on the tissue region and, after positioning the housing, move deployer support plate 24 along axis 53 to position anchor tip 70 onto the tissue region. Anchor tip 70 may, in some examples, penetrate into the tissue region.

In an embodiment, to provide data for monitoring and controlling a medicament injection procedure performed on a tissue region using NeedleTwist 20, at least one (e.g., optical) sensor may be employed for sensing a characteristic of the tissue region. In some examples, the at least one sensor may be configured to image the tissue region, e.g., in the UV, IR and/or visible wavelength range.

Images of the tissue region acquired by an optical sensor and/or an optical fiber may be transmitted to an (e.g., external) processor for processing and/or a display screen for display via a wireless and/or a wire communication channel.

For example, the NeedleTwist 20 and/or housing 26 may comprise at least one sensor and/or at least one optical fiber, for example, configured to image the tissue region. A wire communication channel may be housed at least in part in the wall of housing 26. In some examples, needle cartridge 130 may comprise at least one optical sensor and/or at least one optical fiber (not shown) for imaging the tissue region. In some examples, needle cartridge 130 comprises an optical fiber located on the external surface of, or housed in the lumen of helical needle 140, for imaging internal features of the tissue region during penetration and motion of tip 142 of needle 140 in the tissue region.

Physical quantities sensed by the at least one sensor (e.g., descriptive of images of the tissue region acquired by an optical sensor and/or an optical fiber) may be transmitted to an (e.g., external) processor for processing and/or a display screen for display, for example, via a wireless communication channel and/or a wire channel housed at least partially in housing 132, activation plate 91 or drive screw 52.

An optical fiber may be operably coupled with a sensor and a processor that is configured to process information (e.g., images) relating to a sensed physical quantity such as, for example, radiation, e.g., emitted and/or reflected from the tissue region, for providing a corresponding output via, e.g., a display. For example, an optical fiber on an external surface and/or inside the lumen of helical needle 140 may be coupled by an optical coupler, similar to optical coupler 152, with a matching coupler formed on drive screw 52 for propagation optically or electrically via a wire communication channel along the drive screw to an external processor and/or display. In some examples, a sensed physical quantity may relate to a deformation or displacement of tissue displacement, pressure applied onto the tissue region, and/or the like.

By way of example FIG. 1B schematically shows housing 26 optionally comprising two optical sensors 28 for imaging a tissue region operated on using NeedleTwist 20. Needle cartridge 130 is shown optionally comprising two optical sensors 138 for imaging the tissue region. Helical needle 140 may additionally or alternatively comprise an optical fiber 148 bonded to the outside surface of needle 140. Optical fiber 148 may be employed for imaging internal feature of the tissue region during penetration of the region by the helical needle.

FIGS. 2A-2D schematically illustrate using a NeedleTwist 20 to inject optionally a photosensitizer into a tissue region such as the sclera of a patient's eye 200 and illuminate the injected photosensitizer with suitable radiation provided by radiation source 102, for example, to promote scleral crosslinking and, e.g., moderate elongation of the eye.

The figures schematically show a simplified cross section of eye 200 comprising the sclera 202; cornea 204; limbus 205; iris 206; perimeter 208 of the pupil (also referred to by numeral 208), and lens 210 of the eye.

By way of example, the photosensitizer may comprise at least one or any combination of one or more of: Riboflavin with hydroxypropyl methylcellulose (HPMC) or sodium hydroxymethylglycinate (SMG) (PMID: 31860073) or dextran; UVA or blue light activated Riboflavin; water Soluble Tetrazolium Salt-11 (WST-11) activatable with near infrared (NIR) illumination; Rose Bengal activatable with green light (RGX); and/or Eosin Y (EY, photosensitizer)+triethanolamine (TEOA, initiator)+1-vinyl-2-pyrrolidinone (catalyst) activatable with green light. Biochemical cross linkers that do not require activation by exposure to radiation and may be injected into the eye using NeedleTwist 20 may comprise at least one or any combination of one or more of: Genipin; Microbial transglutaminases (Tgases); Different carbohydrates monosaccharide ribose, disaccharide sucrose, polysaccharide; glycogen; Glyceraldehyde; Methylglyoxal; Decorin; and/or Galacorin.

Figure 2A:
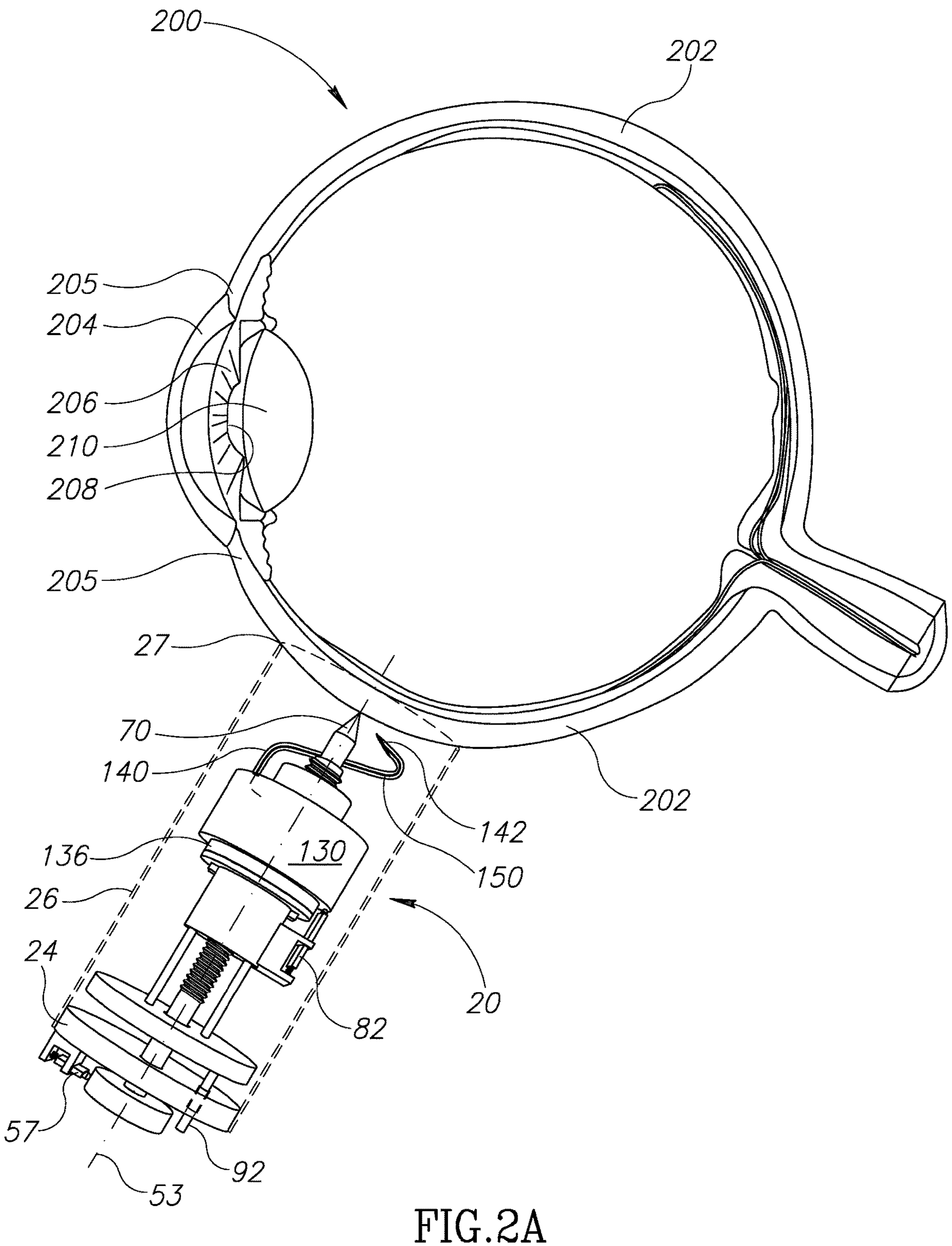
FIGS. 2A-2D schematically illustrate the NeedleTwist shown on FIG. 1B being used by way of example to inject a photosensitizer into the sclera of an eye, in accordance with an embodiment of the disclosure.
Figure 2B:
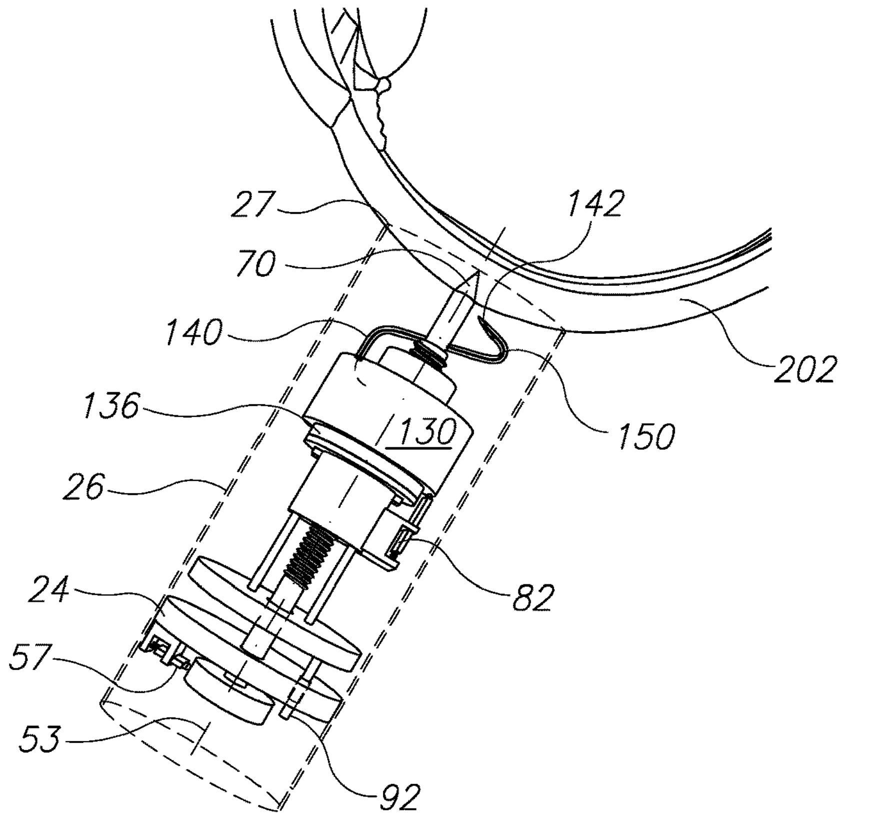

In FIG. 2A, NeedleTwist 20 is placed on eye 200 so that edge surface 27 of housing 26 contacts and seats on sclera 202 of the eye. In the figure, neither anchor tip 70 nor end 142 of helical needle 140 contacts the sclera, and activation button 92 of syringe system 90 (FIGS. 1A and 1B) has not been pushed down to force photosensitizer stored in reservoir 136 out of the reservoir. In FIG. 2B deployer support plate 24 is translated within housing 26 along axis 53 to cause anchor tip 70 to penetrate but not puncture through sclera 202.

Figure 2C:
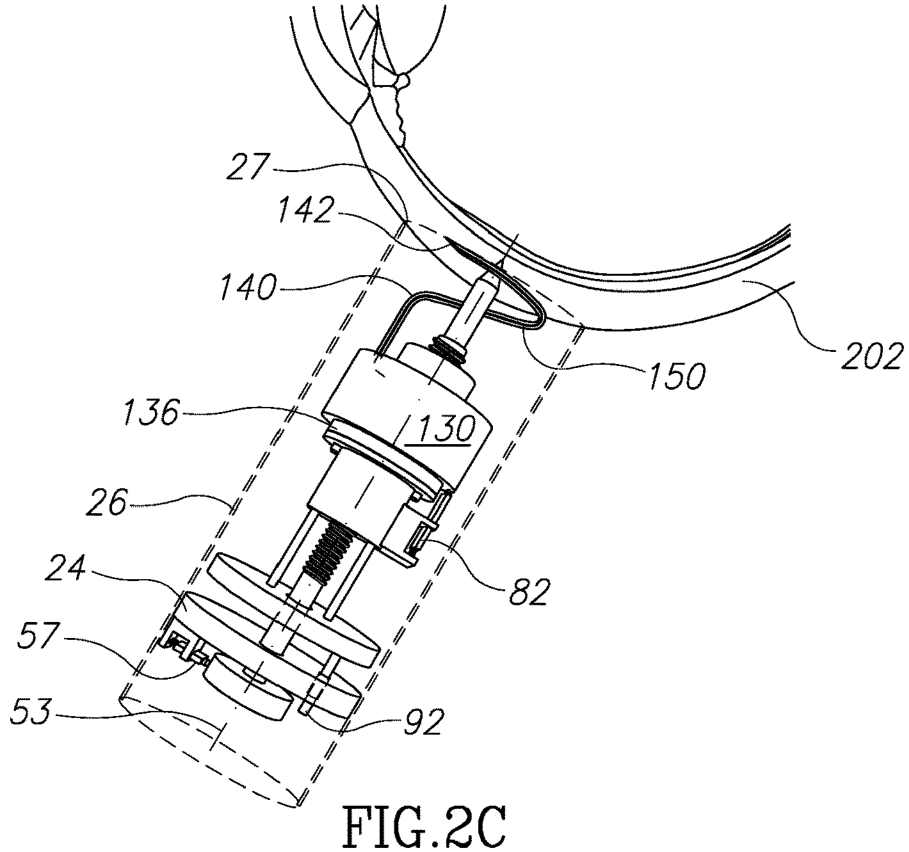
Figure 2D:
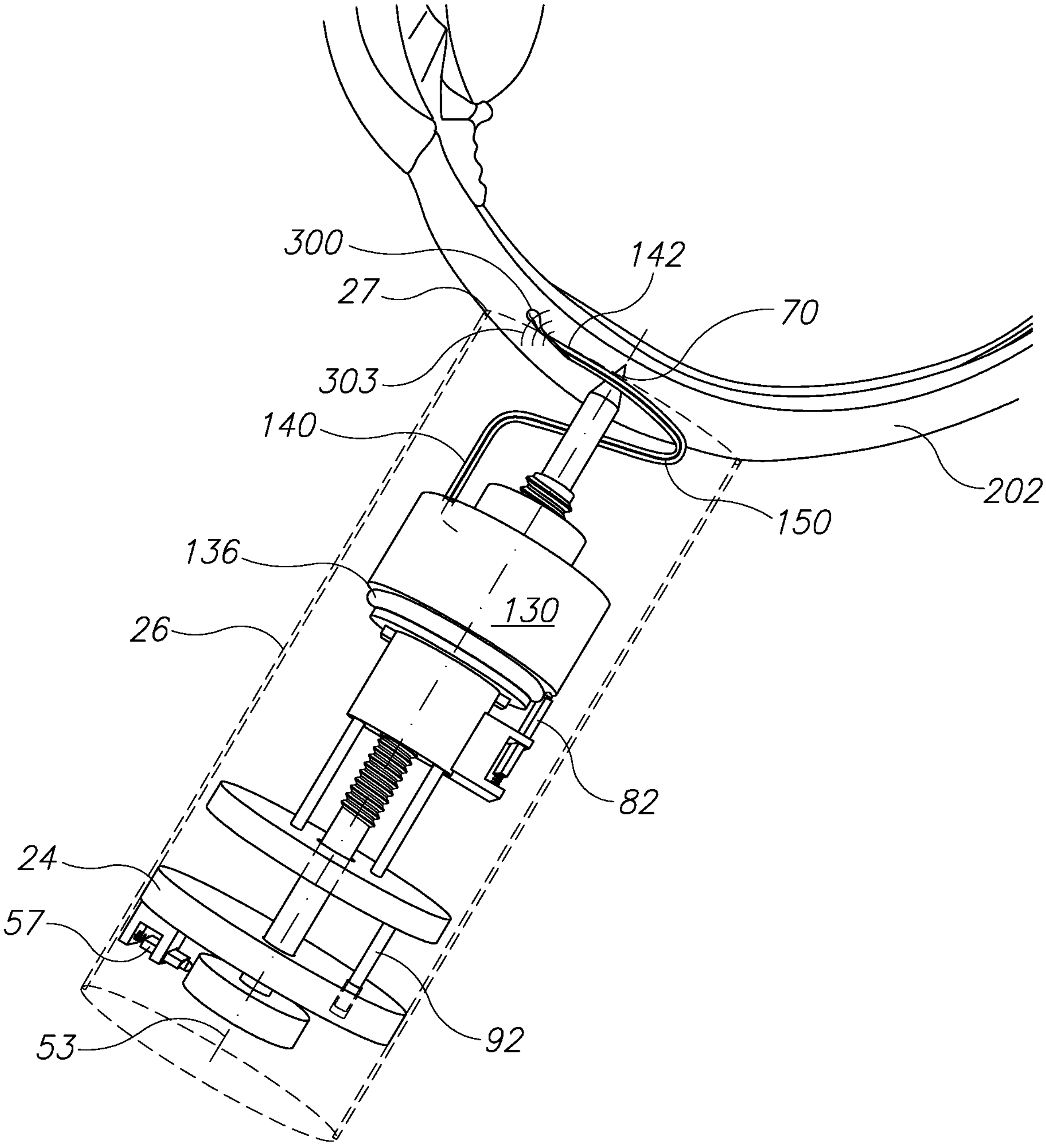

Following penetrating sclera 202 with anchor tip 70, (e.g., piezoelectric) drive screw motor 57 of linear motion screw drive 50 and (e.g., piezoelectric) motor 82 of rotary drive 80 are controlled to translate and rotate needle cartridge 130 to push needle end 142 into sclera 202 along a substantially helical path and position the needle end at a desired location in the sclera. FIG. 2C schematically shows helical needle 140 after operation of screw drive 40 and rotary drive 80 (FIG. 1A) to position needle end 142 at an advantageous location in sclera 202. In FIG. 2D, activation button 92 is depressed to squeeze reservoir 136 and force a bolus 300 of photosensitizer out of the reservoir, through helical needle 140 and out end 142 of the needle into sclera 202. After injecting the bolus of photosensitizer into the sclera, power source 106 of radiation system 100 (FIG. 1A) is controlled to excite radiation source 102 (FIGS. 1A and 1B) to radiate UVA and/or blue light. Optical fiber 150 receives and propagates the radiated electromagnetic radiation to (e.g., illuminate and) activate the injected bolus 300 of photosensitizer. Arcs 303 schematically represent radiation that is radiating from optical fiber 150 to illuminate bolus 300.

Whereas in FIGS. 2A-2D NeedleTwist 20 is schematically shown being used to inject photosensitizer into a region of sclera 202 along a region of the sclera of eye 200 to a side of the eye's cornea 204, in an embodiment a NeedleTwist may be configured and dimensioned to be centered over the cornea and inject photosensitizer in or alongside the limbus of an eye.

Figure 3A:
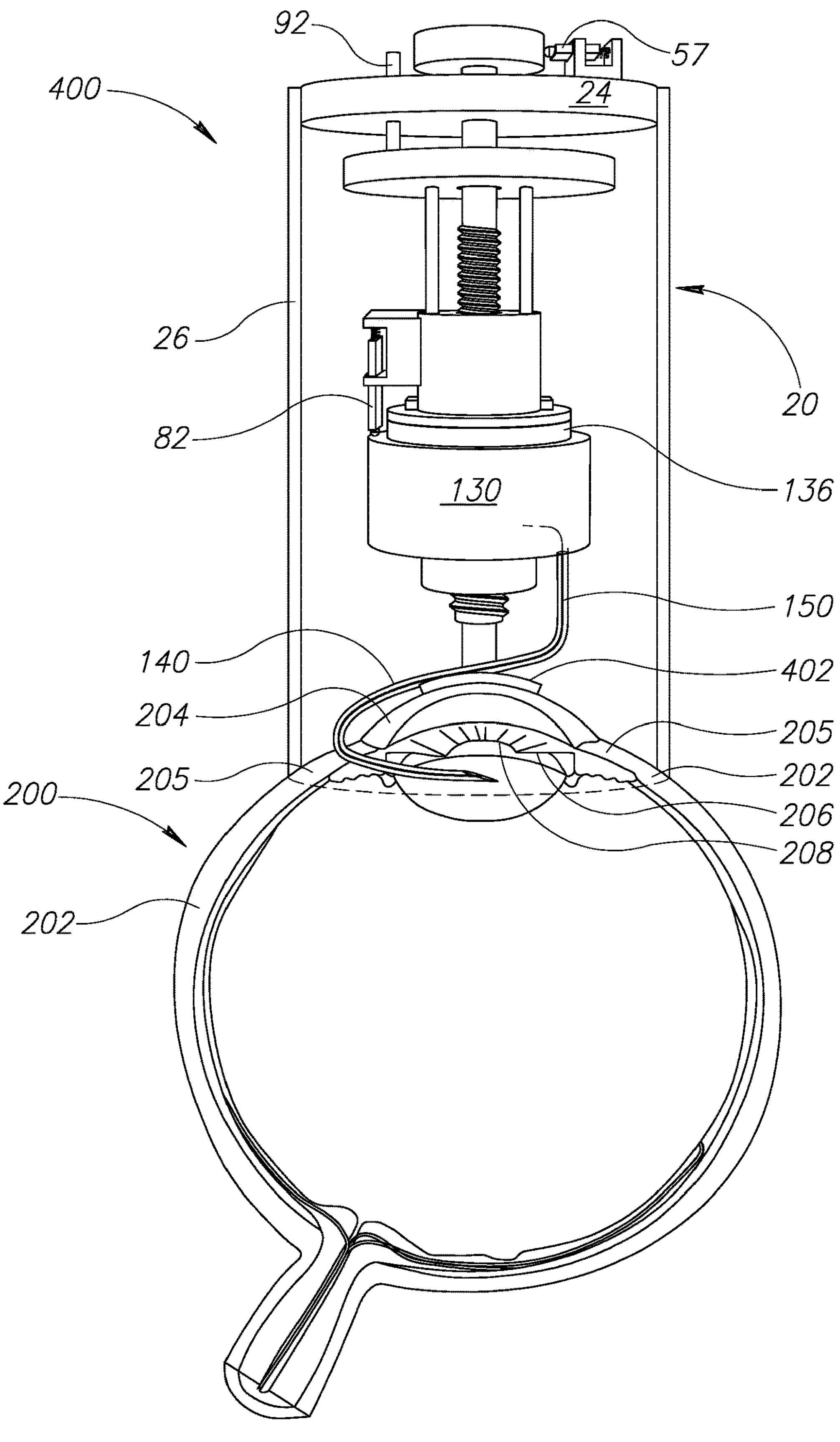
FIG. 3A schematically shows a NeedleTwist adapted for placement over the cornea of the eye, in accordance with an embodiment of the disclosure.

FIG. 3A schematically shows a NeedleTwist 400 being used optionally to inject a photosensitizer into limbus 205 of eye 200. In NeedleTwist 400, contact anchor tip 70 is replaced by a contact anchor cup 402 rotatably mounted to drive shaft 52 and shaped to contact cornea 204, and diameter of housing 26 is dimensioned to placed on or beyond limbus 205.

Figure 3B:
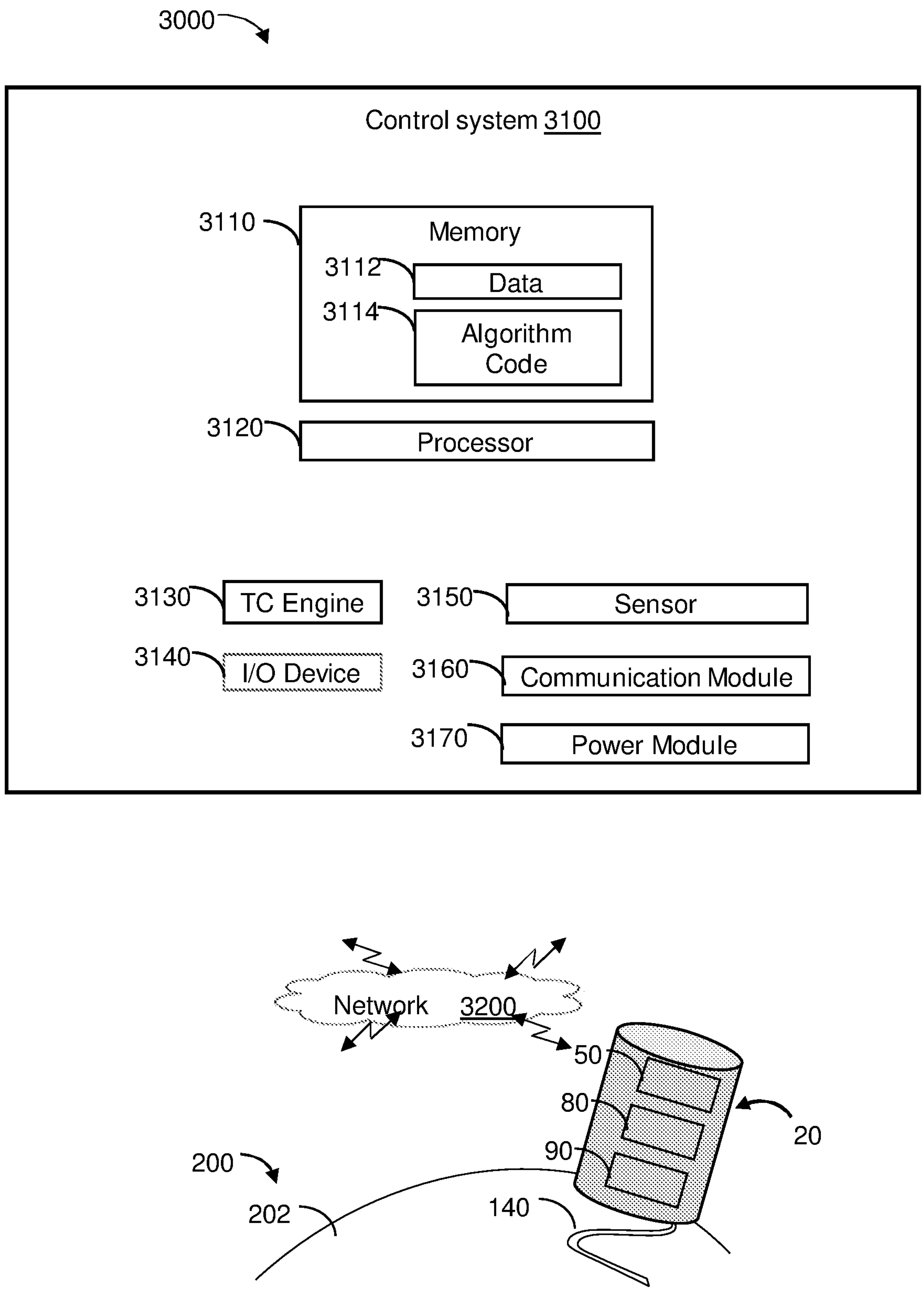
FIG. 3B is a schematic block diagram illustration of a tissue treatment system, in accordance with an embodiment of the disclosure.

Referring now to FIG. 3B, the operation of the NeedleTwist (e.g., NeedleTwist 20) may be controllable, for example, as outlined herein, by a Control system 3100. In some examples, the NeedleTwist may comprise some or all components of Tissue Treatment Control System 3100. A tissue treatment system 3000 may be considered to include both control system 3100 and a NeedleTwist.

In some embodiments, control system 3100 may include a memory 3110 configured to store data 3112 and algorithm code 3114, and a processor 3120. Processor 3120 may be configured to execute algorithm code 3114 for the processing of data 3112 which may result in the implementation of a treatment control (TC) engine 3130.

TC engine 3130 may implement various functionalities of control system 3100, e.g., as outlined herein.

Although some of the components, modules, functional engines and/or processes are shown as being external to the NeedleTwist, this should by no means be construed in a limiting manner. Accordingly, some of the subsystems, devices, components, modules, functional engines and/or processes of the control system 3100 may be run and/or comprised in the NeedleTwist and some may be executable and/or comprised in one or more computing platforms external to the NeedleTwist. However, for simplicity and without be construed in a limiting manner, the description and claims may refer to a single module and/or component.

For example, although processor 3120 may be implemented by several processors, the following description will refer to processor 3120 as the component that conducts all the necessary processing functions of control system 3100.

The one or more computing platforms may include a multifunction mobile communication device also known as "smartphone", a personal computer, a laptop computer, a tablet computer, a server (which may relate to one or more servers or storage systems and/or services associated with a business or corporate entity, including for example, a file hosting service, cloud storage service, online file storage provider, peer-to-peer file storage or hosting service and/or a cyberlocker), personal digital assistant, a workstation, a wearable device, a handheld computer, a notebook computer, a vehicular device and/or a stationary device.

Memory 3110 may be implemented by various types of memories, including transactional memory and/or long-term storage memory facilities and may function as file storage, document storage, program storage, or as a working memory. The latter may for example be in the form of a static random access memory (SRAM), dynamic random access memory (DRAM), read-only memory (ROM), cache and/or flash memory. As working memory, memory 3110 may, for example, include, e.g., temporally-based and/or non-temporally based instructions. As long-term memory, memory 3110 may for example include a volatile or non-volatile computer storage medium, a hard disk drive, a solid state drive, a magnetic storage medium, a flash memory and/or other storage facility. A hardware memory facility may for example store a fixed information set (e.g., software code) including, but not limited to, a file, program, application, source code, object code, data, and/or the like.

The term "processor", as used herein, may additionally or alternatively refer to a controller. Processor 3120 may be implemented by various types of processor devices and/or processor architectures including, for example, embedded processors, communication processors, graphics processing unit (GPU)-accelerated computing, soft-core processors and/or general purpose processors.

In some embodiments, TC engine 3130 may be configured to receive an input via an I/O device 3140 to provide control output for controlling the operation of one or more components, modules, functional engines (e.g., TC engine 3130) and/or processes of treatment system 3000.

In some embodiments, I/O device 3140 may be engaged, e.g., by a user (e.g., a medical professional) of NeedleTwist, for controlling the operation of drive screw motor 57 of linear motion screw drive 50 to cause controlled axial displacement of a needle 140.

In some embodiments, I/O device 3140 may be engaged by the user for controlling cartridge motor 82 of rotary motion drive 80 to cause rotation of the cartridge and thereby of needle 140, which may be coupled with the cartridge.

In some embodiments, input device 3140 may be engaged by the user for controlling activation of syringe system 90, for example, by selective activation of syringe control button, for the controlled release of a desired amount of a medicament stored in the reservoir 136 into a (target) tissue region.

In some embodiments, I/O device 3140 may be engaged to control the emission of radiation by radiation source 102.

In some examples, operation of functionalities of the NeedleTwist may be controlled automatically, semi-automatically or manually.

As an input device, I/O device 3140 may include, for example, device interfaces (e.g., a Universal Serial Bus interface), a touch screen, a keyboard, a keypad, a mouse, a touch-pad, a track-ball, a stylus, a microphone, or other suitable pointing device and/or input device. As an output device, I/O device 3140 may comprise, for example, a display device configured to display one or more images captured by a sensor and include, for example, head mounted display (HMD) device(s), first person view (FPV) display device(s), a monitor, a screen, a touch-screen, a flat panel display, a Light Emitting Diode (LED) display unit, a Liquid Crystal Display (LCD) display unit, a plasma display unit. In some examples, I/O device 3140 may comprise one or more audio speakers or earphones, device interfaces (e.g., a Universal Serial Bus interface), and/or other suitable output devices.

As mentioned herein above, at least one sensor 3150 may be employed, for example, for imaging a tissue region, e.g., before, during and/or after delivering the medicament and/or radiating the tissue region with activation light. The at least one sensor 3150 may be implemented, for example, as discussed herein in FIG. 1B with respect to sensors 28 and sensors 138.

In some embodiments, sensor 3150 may include one or more cameras or imaging devices configured to capture one more images (e.g., a video) of a patient's eye 200 including the tissue region of interest. In some embodiments, the one or more cameras may be configured to image needle, optionally including the needle tip.

In some embodiments, sensor 3150 may include an encoder for sensing an angular and/or linear displacement of the needle.

In some embodiments, sensor 3150 may include one or more pressure sensors for sensing a normal stress and/or shear stress applied, e.g., to a tissue region, by the needle and/or needle tip. In some embodiments, sensor 3150 may include one or more pressure sensors for sensing a normal stress and/or shear stress applied, e.g., by a tissue region, onto the needle and/or needle tip.

In some embodiments, information relating to sensed characteristics of the tissue region may be output via I/O device 3140, for example, to the user of the NeedleTwist. The information output may include images captured by sensor 3150.

In some examples, axial displacement and rotation of the NeedleTwist may be automatically controlled based on a sensed physical quantity (e.g., image information, pressure) relating to a characteristic of the tissue region and/or the needle. For example, a magnitude of an angular and/or translational displacement and/or the angular and/or linear displacement velocity of the needle relative to a tissue region may be controlled based on image data acquired by at least one imaging device, by an encoder of the rotary to linear displacement motors, and/or by a pressure sensor configured to sense, for example, pressure to which the needle may be subjected to.

In some embodiments, a tissue region may be imaged and displayed to the user by I/O device 3140. The user may then provide an input (e.g., mark on a touchscreen), a tissue target engagement position.

In some examples, based on the received input and the present position and orientation of the needle relative to the target tissue engagement position, TC engine 3140 may automatically determine a required angular and linear displacement of the needle 140, and control motors 82 and 52 accordingly.

In some examples, tissue irradiation parameter values (e.g., duration, intensity) may be controlled based on sensed physical quantities such as, for example, acquired images of the tissue region, and/or sensed shear and/or normal stress applied onto the tissue region and/or the needle.

Control system 3100 may further comprise at least one communication module 3160 configured to enable wired and/or wireless communication between the various components and/or modules of the system and/or apparatuses and which may communicate with each other over one or more communication buses (not shown), signal lines (not shown) and/or a network infrastructure 3200.

RF-based wireless communication; optical-based wireless communication such as infrared (IR) based signaling, and/or wired communication. Network infrastructure 3200 may be configured for using one or more communication formats, protocols and/or technologies such as, for example, to internet communication, optical or RF communication, telephony-based communication technologies and/or the like. In some examples, communication module 3160 may include I/O device drivers (not shown) and network interface drivers (not shown) for enabling the transmission and/or reception of data over network infrastructure 3200. A device driver may for example, interface with a keypad or to a USB port. A network interface driver may for example execute protocols for the Internet, or an Intranet, Wide Area Network (WAN), Local Area Network (LAN) employing, e.g., Wireless Local Area Network (WLAN)), Metropolitan Area Network (MAN), Personal Area Network (PAN), extranet, 2G, 3G, 3.5G, 4G, 5G, 6G mobile networks, 3GPP, LTE, LTE advanced, Bluetooth® (e.g., Bluetooth smart), ZigBee™, near-field communication (NFC) and/or any other current or future communication network, standard, and/or system.

Control system 3100 may further include a power module 3170 for powering the various components and/or modules and/or subsystems of the system and/or apparatuses. Power module 3170 may comprise an internal power supply (e.g., a rechargeable or non-rechargeable battery) and/or an interface for allowing connection to an external power supply.

Methods of Delivery

An aspect of the present disclosure relates to a method for delivering a pharmaceutical composition to a desired site in a subject's organ or tissue, using the needle and/or the apparatus described herein for injecting the pharmaceutical composition.

"Pharmaceutical composition", as used herein, refers to a preparation, in which different components, including one or more active agents, are combined. Usually, a pharmaceutical composition comprises one or more pharmaceutically and physiologically acceptable carriers, which can be administered to a subject in a specific form, such as, but not limited to, intravitreal injection. The active agent(s) may be therapeutically active, in which case the pharmaceutical composition is also referred to as a medicament or drug. The active agent(s) may be a contract agent, or a dye and the pharmaceutical composition is also referred to as "a test substance" or a "test composition".

A contemplated method is useful for effecting local delivery of the pharmaceutical composition, which may be, for example, a medicament, a test substance, or a combination thereof, with a desired spatial and temporal resolution.

In some embodiments, a contemplated method is useful for controlled delivery of a bolus of the pharmaceutical composition.

The method for delivery disclosed herein find use in treatment of various medical conditions which may benefit from precise local delivery of, e.g., drugs and/or irradiation to afflicted tissues and/or organs in a subject. By way of example, myopia is a medical condition which may be treated by delivering both a pharmaceutical composition, for example a crosslinking agent that polymerizes upon irradiation, and UVA irradiation to a desired region in a tissue of the eye of the subject, such as to a region of the sclera. The contemplated method of delivery employing, for example, NeedleTwist, may enable bolus delivery of a medicament to the sclera.

When a test compound such a dye, a contrast agent, and imaging agent and the like, is delivered, the contemplated method may be useful for assessing feasibility of precise local drug delivery, thus, enabling monitoring and controlling a medicament injection procedure before it is performed on a desired tissue region.

EXAMPLES

Example 1

Testing Feasibility of Delivery

To test the ability of the delivery device described herein, exemplified by the NeedleTwist, to effect local delivery of a pharmaceutical composition to a tissue, more specifically to demonstrate efficacy of delivery of a test compound to a desired scleral tissue and to determine the distribution of the compound in the sclera, the delivering of a dye to the desired scleral tissue was assessed. For this purpose, live New Zealand white (NZW) rabbits were injected with indocyanine green (ICG) dye (a cyanine fluorophore and optical imaging agent (pre) clinically used for near infra-red (NIR) fluorescence imaging in medical diagnostics) by setting the NeedleTwist at a position of about 3 mm to the limbus and injecting the dye. An exemplary injection process is demonstrated in FIGS. 4A-4D.

It is noted that alternative configurations may be conceived where, for example, the point of injection may be different than what is illustrated in FIGS. 4A-D. For instance, a comparatively larger coil may be employed configured to rotate around a twist axis at the level of the equator or anterior or posterior to it. In some examples, the anchor axis may be at the center or substantially at the center of the cornea.

Immediately after injection, the rabbits were sacrificed, the injected eyes were enucleated, and the sclera was assessed for green fluorescence. As shown in an exemplary tested eye presented in FIG. 4E, the ICG dye covered about 30% of the area of the back of the eye, as expected.

These results further demonstrate the utility of NeedleTwist in monitoring and controlling a medicament injection procedure performed on a tissue region.

Example 2

Local Delivery of Riboflavin A to Scleral Tissue

The ability of NeedleTwist to effect local delivery and activation of a medicament, while providing a desired degree of spatial and temporal resolution, was assessed by injecting riboflavin A to a scleral tissue, subsequently followed by delivery of polymerizing irradiation (also termed herein "curing irradiation") to the locus of medicament delivery.

Live rabbits were injected with a pharmaceutical composition comprising riboflavin A (isotonic solution comprising 0.1% Riboflavin and 20% Dextran 500) using a NeedleTwist device described herein. Immediately after injection, UVA irradiation was delivered for a period of 30 minutes using the same NeedleTwist device. In each rabbit, only one eye was injected with the photosensitizer and then irradiated with UVA. The second eye was not treated and served as control of the injection process, as demonstrated in FIG. 5.

After 12 hours, the rabbits were sacrificed, and the eyes were enucleated. Scleral pieces (~3 mm×3 mm) were cropped from both treated and untreated eyes, photographed and weighed (using analytic scales).

Figure 6:
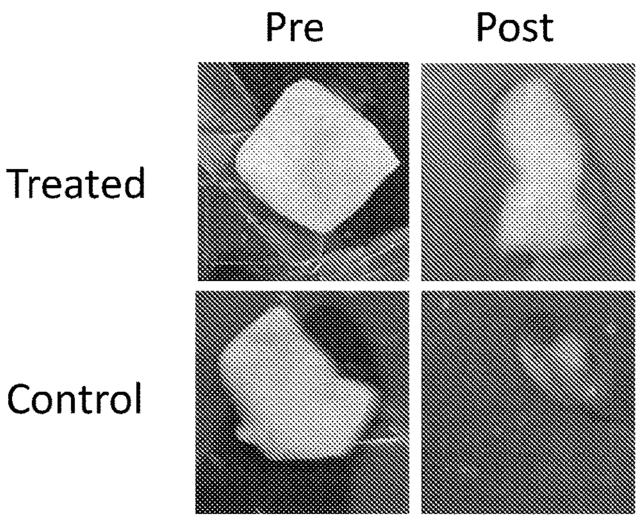
FIG. 6 are photographs of exemplary scleral pieces taken from an eye of a rabbit treated with riboflavin A and UVA irradiation using a NeedleTwist device, and from the contralateral eye which was not treated (control). The scleral pieces were photographed before (Pre) and after (Post) incubation with Collagenase A for 7 hours at 37° C.

To assess effective crosslinking of scleral collagen following injection of riboflavin and UVA irradiation, scleral pieces of both treated and control eyes were subjected to digestion by Collagenase A. For this purpose, 11-12 scleral pieces were incubated with Collagenase A (3.48 mg/ml, 1677 U/ml) for 7 hours at 37° C. Remaining (undigested) pieces were photographed & weighed (analytic scales). Photographs of exemplary riboflavin-treated and control pieces taken before and after incubation with Collagenase are shown in FIG. 6.

None of the 12 riboflavin-treated scleral pieces were digested by collagenase, whereas 4 out of 11 (36%) control pieces were completely digested.

Figure 7:
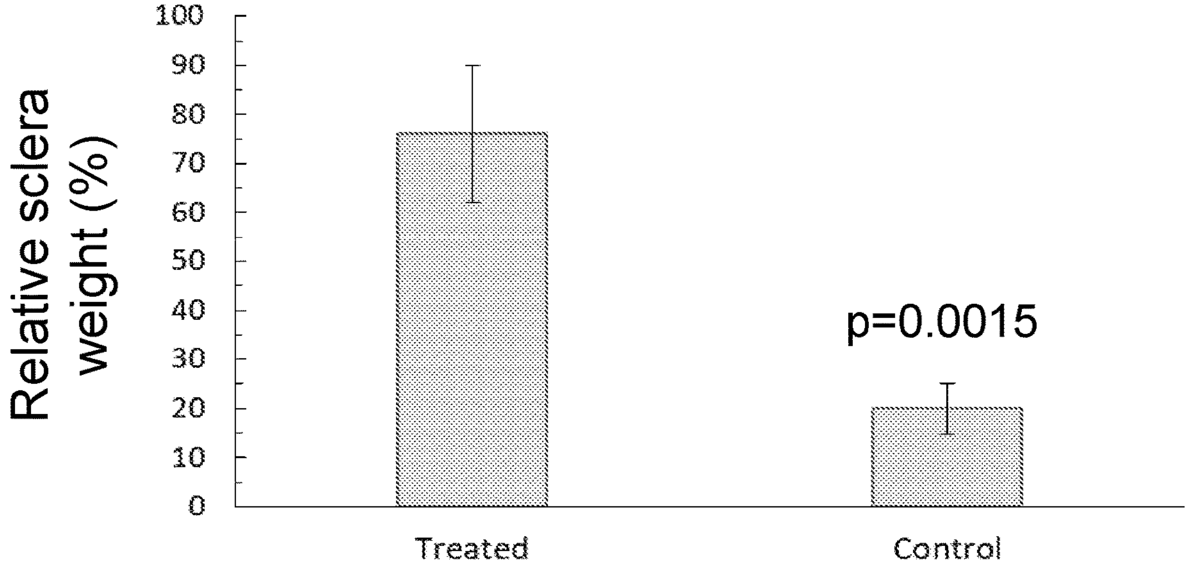
FIG. 7 is a bar graph showing the relative weight of scleral pieces of eyes of rabbits treated with riboflavin A and UVA irradiation using a NeedleTwist device, and eyes which was not treated (control), following 7 hours incubation with Collagenase A at 37° C.

As seen in FIG. 7, treated sclera tissues were substantially heavier than corresponding untreated tissues, indicating resistance to enzymatic digestion due to effective cross-linking. Eyes not receiving treatment were nearly completely digested (20% of original weight), whereas eyes receiving treatment using a NeedleTwist device described herein were resistant to digestion due to scleral cross-linking and maintained nearly 80% of original weight (p=0.0015).

The results disclosed in Examples 1 and 2 clearly demonstrate that the delivery apparatus or device of the present disclosure is useful for obtaining a desired spatial and temporal resolution local delivery of a pharmaceutical composition as well as monitoring and controlling the injection procedure performed in the tissue.

Additional Examples

An aspect of an embodiment of the disclosure relates to providing device for controlled delivery of a bolus of a medicament to a tissue region. In accordance with an example of the disclosure, the device, also referred to as a NeedleTwist medicament delivery device, or simply NeedleTwist device or NeedleTwist, comprises a hollow needle, optionally configured as a helical needle, curved at least in part to have contorted shape of, for example, a helix having a twist axis for injecting into a tissue region a medicament contained in a reservoir coupled with the needle. NeedleTwist comprises a needle deployment apparatus, also referred to as a "deployer", coupled with the helical needle and a syringe system coupled with the reservoir.

In some examples, the deployer is operable to independently translate the needle along the twist axis and/or rotate the needle about the twist axis to deploy and position a tip of the needle in a desired target location inside the tissue region. In some examples, the needle can be selectively axially translated in proximal direction towards the tissue region and in distal direction away from the tissue direction. In some examples, independent from the translational displacement, the needle can be selectively rotated in clockwise and counterclockwise direction.

In some examples, the needle having a lumen has a distal opening for delivery medicament to the tissue region. In some additional examples, the needle has one or more lateral openings, apertures or orifices that are laterally extending through the needle wall for delivery of a medicament to the tissue region.

When advantageously deployed, the syringe system may be operated to force medicament from the reservoir into the needle and out from the needle tip into the tissue region.

In an embodiment, NeedleTwist comprises a stabilizer configured to stabilize position of the deployer and thereby to stabilize position and motion of the helical needle during use of NeedleTwist to deliver medicament to the tissue region. Optionally, the stabilizer comprises a housing that houses the deployer, and, for example, a contact anchor.

In some examples, the housing may be formed having a surface configured to be placed on or adjacent to the tissue region, and the contact anchor is configured to contact the tissue region or adjacent tissue to facilitate preventing motion of the housing relative to the tissue region when advantageously positioned on or adjacent the tissue region.

In an example, NeedleTwist may comprise a radiation delivery system for delivering radiation advantageous for facilitating delivery and/or activation of the medicament to or in the tissue region. Optionally, the radiation delivery system comprises an optical fiber housed in the helical needle that propagates the radiation from a source of the radiation to the tissue region.

In an example, the helical needle may comprise in a disposable needle cartridge that may be mounted to the deployer for use in delivering the medicament and thereafter may be dismounted for disposal. Optionally, the needle cartridge comprises a reservoir prefilled with the medicament.

In an example, NeedleTwist may be configured to deliver a scleral crosslinking medicament comprising a photosensitizer to a region of the sclera of a patient's eye. The radiation delivery system is configured to irradiate a bolus of the delivered photosensitizer with radiation that activates the photosensitizer.

Further Examples

Examples concern a device for injecting a medicament into a tissue. The device is configured such that medicament can be injected at a desired depth into the tissue region, allowing delivery of treatment light through an encapsulating tissue layer or by making a comparatively small hole through the encapsulating tissue layer for treatment of a tissue region underlying the encapsulating tissue layer. Furthermore, the device may facilitate or be configured to dissect tissue underlying the encapsulating tissue layer for treatment of a target tissue region allowing, for example, impregnation and delivery of the medicament to the target tissue region.

In some embodiments, the device may be configured such that the magnitude of a translational distance to be traversed by a needle can be automatically, semi-automatically or manually controlled. Translational resolutions may be, for example, 100 microns or less, 75 microns or less, or 50 microns or less, or 10 microns or less, to facilitate, for example, controlled translational positioning of the needle tip, e.g., relative to a tissue surface, for the release of a medicament into the tissue region (e.g., conjunctiva) via the needle at a desired depth relative to the tissue surface.

In some embodiments, the device may be configured such that the magnitude of angular distance to be traversed by a needle can be automatically, semi-automatically or manually controlled. In some examples, the controllable angular rotational resolution of a twist axis may be, for example, 10 degrees or less, 5 degrees or less, or 1 degree or less, to facilitate, for example, controlled angular positioning of the needle tip relative to a reference axis for the release of a medicament dose into tissue region (e.g., the conjunctiva) via the needle at a desired angular position.

In Example 1, the device may comprise a rotary motion drive having a motion drive rotary axis and which is configured to receive a needle and operable to rotate the needle about the motion drive rotary axis; and a linear motion drive comprising a drive screw and configured to translate the needle selectively in either proximal and distal direction along a translation axis, and further configured such that, when the device is operably engaged with the tissue, the drive screw remains translationally stationary relative to the tissue during operation of the rotation motion drive to longitudinally translate the needle. The rotary motion drive and the linear motion drive may be independently operatable.

In Example 2, the subject matter of Example 1 may optionally further comprise wherein the rotary motion drive is configured to receive a straight needle having a needle axis such that the needle axis is offset relative to the motion drive rotary, the contact anchor axis.

In Example 3, the subject matter of any one or more of examples 1-2 may optionally further comprise wherein the rotary motion drive is configured to receive a contorted needle having a twist axis such that the twist axis coincides or substantially coincides with the motion drive rotary axis.

In Example 4, the subject matter of any one or more of the examples 1-3 may optionally further comprise, wherein the screw drive is operably engagable to cause rotation of the drive screw.

In Example 5, the subject matter of any one or more of the examples 1 to 4 may optionally further comprise a contact anchor for contacting the tissue region to stabilize the position of the apparatus relative to the tissue region and/or delimit the depth of injection by the injection needle. In some examples, the housing may constitute that contact anchor. In some examples, the housing may include the contact anchor, instead or in addition to being part of the drive screw.

In example 6, the subject matter of example 5 may optionally further comprise, wherein the contact anchor is formed having a pointed end for penetrating the tissue region, a surface shaped to match and lie on the region of tissue or a cup-like end for facilitating suction-based engagement of the contact anchor with the tissue.

In example 7, the subject matter of any one or more of the examples 1 to 6 may optionally further comprise a drive stage that is threaded with the screw drive for selectively translationally drive the drive stage in one of a proximal and a distal direction.

In example 8, the subject matter of any one or more of the examples 1 to 7 may optionally further comprise a needle cartridge housing. Optionally, the needle cartridge housing may be rotatably coupleable with the drive stage to allow rotation of the needle cartridge by the rotary motion drive relative to the drive stage.

In example 9, the subject matter of example 8 may optionally further comprise wherein the rotary motion drive comprises at least one motor operably coupled with, e.g., a surface, of the cartridge housing to rotate the cartridge housing and thereby a needle receivable by the cartridge housing about an axis of rotation substantially coincident with the translational axis.

In example 10, the subject matter of any one or more examples 8 to 9 may optionally further comprise wherein the needle cartridge housing comprises a reservoir configured to contain the medicament.

In example 11, the subject matter of example 10 may optionally further comprise, wherein the reservoir includes a receptacle configured to receive medicament, or is formed from or includes a compressible material configured to receive the medicament.

In example 12, the subject matter of any one or more of examples 10-11 may optionally further comprise, wherein the device comprises a syringe system operable to engage with the reservoir to push medicament stored in the reservoir into the needle and out from the needle to deliver a quantity of the medicament to the tissue region.

In example 13, the subject matter of any one or more of examples 1 to 12 may optionally further comprise a radiation delivery system operable to irradiate radiation for illuminating the tissue region.

In example 14, the subject matter of example 13 may optionally further comprise a source of the radiation; an optical fiber optically coupled with the radiation source of the radiation to receive radiation emitted by the radiation source and to deliver received radiation to needle orifice(s).

In example 15, the subject matter of example 14 may optionally further comprise, wherein one or more optical fibers are housed inside the lumen of the needle and/or mounted to an external surface region of the needle.

In Example 16, the subject matter of any one or more of the examples 1 to 15 may optionally further comprise, wherein the device further comprises a housing configured to house the linear and rotary motion drives, the syringe system, and radiation system. Optionally, the radiation delivery system can also receive radiation reflected from the tissue region for tissue analysis by a sensor.

In Example 17, the subject matter of example 16 may optionally further comprise wherein the housing is configured to seat on or near to the tissue region.

Example 18 concerns a needle for injecting a medicament into a tissue, the needle comprising: a hollow tube formed to a shape of a helix having a twist axis, the hollow tube having an input orifice for receiving a medicament at a first end of the tube and an output orifice for release of the received medicament at a second end of the tube, which second end is formed pointed to facilitate penetration of the second end into a region of tissue.

In Example 19, a device or apparatus for injecting a medicament into a tissue comprises a rotary motion drive that can be coupled with the needle of example 18 and operable to rotate the needle about the needle twist axis.

In Example 20, the subject matter of example 19 may optionally further comprise a linear motion drive operable to translate a needle selectively in either direction along the needle twist axis.

In example 21, the subject matter of example 20 may optionally further comprise wherein the linear motion drive comprises a screw drive for moving a needle along the needle twist axis.

In example 22, the subject matter of example 21 may optionally further comprise a drive screw having a drive screw axis substantially coincident with the twist axis;

a drive stage threaded onto the drive screw;

at least one drive screw motor operable to selectively rotate the drive screw clockwise or counterclockwise about the drive screw axis to translate the drive stage along the drive screw axis. The drive stage can be coupled with the needle.

In example 23, the subject matter of example 22 may optionally further comprise, wherein the screw drive comprise a transmission head fixed to the drive screw and coupled with the at least one drive screw motor so that the drive screw motor is controllable to rotate the transmission head and thereby the drive screw.

In example 24, the subject matter of examples 22 and/or 23 may optionally further comprise wherein the drive screw motor is a piezoelectric motor friction coupled with the transmission head In example 25, the subject matter of any one or more of the examples 19 to 24 may optionally further comprise, a contact anchor tip, e.g., at a distal end of the drive screw for contacting the tissue region to stabilize the position of the apparatus relative to the tissue region.

In example 26, the subject matter of example 25 may optionally further comprise a bearing mounted to the distal end of the drive screw.

In example 27, the subject matter of examples 25 and/or 26 may optionally further comprise wherein the contact anchor tip is formed having a receiving groove matched to the bearing and is rotatably mountable to the drive screw by pushing the contact anchor tip onto the bearing to snap catch the bearing in the groove.

In example 28, the subject matter of any one or more of examples 25 to 27 may optionally further comprise wherein the contact anchor tip is formed having a pointed end for penetrating the tissue region.

In example 29, the subject matter of any one or more of examples 25 to 28 may optionally further comprise, wherein the contact anchor tip comprises a surface shaped to match and lie on the region of tissue.

In example 30, the subject matter of any one or more of examples 19 to 29 may optionally further comprise a needle cartridge housing that is rotatably mountable to the drive stage and configured for coupling couple a needle with the linear motion drive.

In example 31, the subject matter of example 30 may optionally further comprise wherein the rotary motion drive rotates the needle cartridge housing to rotate the needle about the twist axis.

In Example 32, the subject matter of any one or more of examples 19 to 31 may optionally further comprise wherein the rotary motion drive comprises at least one motor coupled with the cartridge (e.g., to a surface of the cartridge housing) to rotate the cartridge (housing) and thereby the needle about an axis of rotation substantially coincident with the twist axis.

In Example 33, the subject matter of any one or more of the examples 30 to 32 may optionally further comprise, wherein the needle cartridge housing comprises a reservoir configured to contain a fluid medicament.

In example 34, the subject matter of any one or more of the examples 19 to 33 may optionally further comprise, wherein the apparatus comprises a syringe system operable to squeeze the reservoir to push medicament stored in the reservoir into the needle and out from the needle to deliver a quantity of the medicament to the tissue region.

In example 35, the subject matter of any one or more of the examples 19 to 34 may optionally further comprise a radiation delivery system operable to irradiate radiation for illuminating the tissue region.

In example 36, the subject matter of example 35 may optionally further comprise a source of the radiation mounted to the drive screw;

an optical coupler comprised in the needle cartridge housing configured to optically couple with and receive activation radiation radiated by the source of radiation when the needle cartridge housing is mounted to the drive screw;

an optical fiber optically coupled with the optical coupler that receives the received radiation and delivers activation radiation to the second end of the needle.

In example 37, the subject matter of example 36 may optionally further comprise, wherein the optical fiber is housed inside the lumen of the needle and/or coupled with the needle.

In example 38, the subject matter of examples 36 and/or 37 may optionally further comprise wherein the optical fiber is mounted to an external surface region of the needle.

In example 39, the subject matter of any one or more of examples 19-38 may optionally further comprise a housing that houses the linear and rotary motion drives, the syringe system, and radiation system.

In example 40, the subject matter of any one or more of the examples 19 to 39 may optionally further comprise, wherein the housing is configured to seat on or near to the tissue region.

In example 41, the subject matter of any or more of the examples 19 to 40 may optionally comprise, wherein the tissue region is a region of the sclera of an eye.

Example 42 pertains to a method for delivering a pharmaceutical composition to a subject's organ or tissue, comprising injecting the pharmaceutical composition to the subject's organ or tissue with the needle and/or the apparatus according to any one or more of examples 1 to 41

In Example 43, the subject matter of Example 42 may optionally comprise controlled delivery of a bolus of the pharmaceutical composition.

In example 44, the subject matter of examples 42 and/or 43 may optionally comprise, wherein the pharmaceutical composition is at least one of: a medicament, a test substance, or a combination thereof.

In example 45, the subject matter of any one or more examples 42 to 44 may optionally further comprise treatment of a medical condition in the subject.

In example 46, the subject matter of example 45 may optionally comprise, wherein the medical condition is myopia, and the pharmaceutical composition is delivered to a desired region in a tissue of the eye of the subject, such as to a region of the sclera.

In example 47, the subject matter of example 46 may optionally further comprise, wherein the pharmaceutical composition is a medicament delivered to the sclera, for example in bolus delivery.

In Example 48, the subject matter of example 44 may optionally further comprise, wherein the pharmaceutical composition is a test substance, delivered for monitoring and controlling a medicament injection procedure performed on a tissue region.

In example 49, the subject matter of example 44 may optionally further comprise, wherein the test substance is an imaging agent, a dye or a combination thereof.

In example 50, the subject matter of any one or more of the examples 42 to 49 may optionally comprise, wherein the pharmaceutical composition is delivered to the subject's organ or tissue in combination with delivery of radiation thereto.

In example 51, the subject matter of example 50 may optionally comprise, wherein the pharmaceutical composition is a scleral crosslinking medicament.

In example 52, the subject matter of example 51 may optionally comprise, wherein the scleral crosslinking medicament is a photosensitizer.

Example 53 pertains to a method for delivering a medicament to a region of the sclera of a subject's eye subsequently followed by radiation delivery to irradiate the delivered medicament, comprising setting and operating the apparatus and/or needle according to embodiments of the present invention, on or near the region in the scleral tissue.

In Example 54, the subject matter of example 53 may optionally include, for example, delivering a scleral crosslinking medicament comprising a photosensitizer to a region of the sclera of a subject's eye, subsequently followed by radiation delivery to irradiate the delivered photosensitizer with radiation that activates the photosensitizer.

In Example 55, the subject matter of any one or more of the examples 42 to 54 may optionally comprise, a method for effecting local delivery of the pharmaceutical composition and/or medicament with a desired spatial and temporal resolution.

Example 56 pertains to a tissue treatment system, comprising:

at least one sensor;

at least one memory for storing data and software code instructions; and at least one processor configured to process data in accordance with the software code instructions to cause the apparatus of the present invention to perform the following:

sensing, by the at least one sensor, at least one physical quantity relating to a characteristic of tissue region and/or a needle; and controlling, based on the sensed at least one physical quantity, the operation of the linear motion drive and/or the rotary motion drive for operably engaging the needle with the tissue region and/or tissue irradiation parameters.

In example 57, the subject matter of example 56 may optionally further comprise, once the needle is operably engaged with the tissue region, controlling operation of the syringe system for the injection of a desired amount of a medicament into the tissue region.

The terms "device" and "apparatus" may herein be used interchangeably.

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which it is intended.

Wherever a general term in the disclosure is illustrated by reference to an example instance or a list of example instances, the instance or instances referred to, are by way of non-limiting example instances of the general term, and the general term is not intended to be limited to the specific example instance or instances referred to.

The phrase "in an embodiment", whether or not associated with a permissive, such as "may", "optionally", or "by way of example", is used to introduce for consideration an example, but not necessarily a required configuration of possible embodiments of the disclosure. Unless otherwise indicated, the word "or" in the description and claims is considered to be the inclusive "or" rather than the exclusive or, and indicates at least one of, or any combination of more than one of items it conjoins.

Positional terms such as "upper", "lower" "right", "left", "bottom", "below", "lowered", "low", "top", "above", "elevated", "high", "vertical" and "horizontal" as well as grammatical variations thereof as may be used herein do not necessarily indicate that, for example, a "bottom" component is below a "top" component, or that a component that is "below" is indeed "below" another component or that a component that is "above" is indeed "above" another component as such directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both.

"Coupled with" means indirectly or directly "coupled with".

It is important to note that the method may include is not limited to those diagrams or to the corresponding descriptions. For example, the method may include additional or even fewer processes or operations in comparison to what is described herein. In addition, embodiments of the method are not necessarily limited to the chronological order as illustrated and described herein.

It should be noted that the term "light" as used herein may refer to electromagnetic radiation of any suitable wavelength for the purposes of the applications disclosed herein. Accordingly, the term "light" should not be construed as being limited to visible light and may additionally or alternatively include non-visible radiation such as, for example, laser light in the infrared range and UV light.

Accordingly, the term “light” should not be construed as being limited to visible light and may additionally or alternatively include non-visible radiation such as, for example, light in the infrared range, light in the short wave infrared range and light in the ultra-violate range. The light may be coherent, non-coherent or partially coherent. The light may be polarized, non-polarized or partially polarized. The light may have a wide spectral width (e.g., of the range of hundreds of nanometers such as originated from a black body), the light may have a mid-spectral width (e.g. of the range of tens of nanometers such as originated from a LED) or the light may have a narrow spectral width (e.g. of the range of a few nanometers such as originated from a laser). Moreover, the terms “light” and “electromagnetic radiation” may herein be used interchangeably.

Unless otherwise stated or applicable, the use of the expression “and/or” between the last two members of a list of options for selection indicates that a selection of one or more of the listed options is appropriate and may be made, and may be used interchangeably with the expressions “at least one of the following”, “any one of the following” or “one or more of the following”, followed by a listing of the various options.

As used herein, the phrase “A,B,C, or any combination of the aforesaid” should be interpreted as meaning all of the following: (i) A or B or C or any combination of A, B, and C, (ii) at least one of A, B, and C; and (iii) A, and/or B and/or C. This concept is illustrated for three elements (i.e., A,B,C), but extends to fewer and greater numbers of elements (e.g., A, B, C, D, etc.).

The term “tissue region” can include, for example, a treatment site; a surgical site; a diagnostic site; a cosmetic surgery site; and/or any site in the patient’s body that can be invasively accessed with or without requiring incision.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases “ranging/ranges between” a first indicate number and a second indicate number and “ranging/ranges from” a first indicate number “to” a second indicate number are used herein interchangeably and are meant to include the first and second indicated numbers and all the fractional and integral numerals therebetween.

It is important to note that the methods described herein and illustrated in the accompanying diagrams shall not be construed in a limiting manner. For example, methods described herein may include additional or even fewer processes or operations in comparison to what is described herein and/or illustrated in the diagrams. In addition, method steps are not necessarily limited to the chronological order as illustrated and described herein.

Any digital computer system, unit, device, module and/or engine exemplified herein can be configured or otherwise programmed to implement a method disclosed herein, and to the extent that the system, module and/or engine is configured to implement such a method, it is within the scope and spirit of the disclosure. Once the system, module and/or engine are programmed to perform particular functions pursuant to computer readable and executable instructions from program software that implements a method disclosed herein, it in effect becomes a special purpose computer particular to embodiments of the method disclosed herein. The methods and/or processes disclosed herein may be implemented as a computer program product that may be tangibly embodied in an information carrier including, for example, in a non-transitory tangible computer-readable and/or non-transitory tangible machine-readable storage device. The computer program product may directly loadable into an internal memory of a digital computer, comprising software code portions for performing the methods and/or processes as disclosed herein.

The methods and/or processes disclosed herein may be implemented as a computer program that may be intangibly embodied by a computer readable signal medium. A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a non-transitory computer or machine-readable storage device and that can communicate, propagate, or transport a program for use by or in connection with apparatuses, systems, platforms, methods, operations and/or processes discussed herein.

The terms “non-transitory computer-readable storage device” and “non-transitory machine-readable storage device” encompasses distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by one or more communication networks.

These computer readable and executable instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable and executable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable and executable instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The term “engine” may comprise one or more computer modules, wherein a module may be a self-contained hardware and/or software component that interfaces with a larger system. A module may comprise a machine or machines executable instructions. A module may be embodied by a circuit or a controller programmed to cause the system to implement the method, process and/or operation as disclosed herein. For example, a module may be implemented as a hardware circuit comprising, e.g., custom VLSI circuits or gate arrays, an Application-specific integrated circuit (ASIC), off-the-shelf semiconductors such as logic chips, transistors, and/or other discrete components. A module may also be implemented in programmable hardware devices such as field programmable gate arrays, programmable array logic, programmable logic devices and/or the like.

Discussions herein utilizing terms such as, for example, “processing”, “computing”, “calculating”, “determining”, “establishing”, “analyzing”, “checking”, “estimating”, “deriving”, “selecting”, “inferring” or the like, may refer to operation(s) and/or process(es) of a computer, a computing platform, a computing system, or other electronic computing device, that manipulate and/or transform data represented as physical (e.g., electronic) quantities within the computer’s registers and/or memories into other data similarly represented as physical quantities within the computer’s registers and/or memories or other information storage medium that may store instructions to perform operations and/or processes. The term determining may, where applicable, also refer to “heuristically determining”.

Descriptions of embodiments of the invention in the present application are provided by way of example and are not intended to limit the scope of the invention. The described embodiments comprise different features, not all of which are required in all embodiments. Some embodiments utilize only some of the features or possible combinations of the features. Variations of embodiments of the invention that are described, and embodiments comprising different combinations of features noted in the described embodiments, will occur to persons of the art. The scope of the invention is limited only by the claims.

What is claimed is:

1. An apparatus for injecting a medicament into a tissue, the apparatus comprising:

a rotary motion drive having a motion drive rotary axis and which is configured to receive a needle and operable to rotate the needle about the motion drive rotary axis; and a linear motion drive comprising a drive screw and configured to translate the needle selectively in either proximal and distal direction along a translation axis, and further configured such that, when the apparatus is operably engaged with the tissue, the drive screw remains translationally stationary relative to the tissue during operation of the rotation motion drive to longitudinally translate the needle; and wherein the rotary motion drive and the linear motion drive are independently operatable.

2. The apparatus of claim 1, wherein the rotary motion drive is configured to receive a straight needle having a needle axis such that the needle axis is offset relative to the motion drive rotary axis.

3. The apparatus of claim 1, wherein the rotary motion drive is configured to receive a contorted needle having a twist axis such that the twist axis coincides or substantially coincides with the motion drive rotary axis.

4. The apparatus of claim 1, wherein the screw drive is operably engagable to cause rotation of the drive screw.

5. The apparatus of claim 1, further comprising a contact anchor for contacting the tissue region to stabilize the position of the apparatus relative to the tissue region.

6. The apparatus of claim 1, further comprising a drive stage that is threaded with the screw drive for selectively translationally drive the drive stage in one of a proximal and distal direction.

7. The apparatus of claim 1, further comprising a needle cartridge housing that is rotatably coupleable with the drive stage to allow rotation of the needle cartridge by the rotary motion drive relative to the drive stage.

8. The apparatus according to claim 7, wherein the rotary motion drive comprises at least one motor operably coupled with a cartridge housing to rotate the cartridge housing and thereby a needle receivable by the cartridge housing about an axis of rotation substantially coincident with the translational axis.

9. The apparatus according to claim 7, wherein the needle cartridge housing comprises a reservoir configured to contain the medicament.

10. The apparatus according to claim 9, wherein the reservoir is formed from or includes a compressible material configured to receive medicament.

11. The apparatus according to claim 10, wherein the apparatus comprises a syringe system operable to engage with the reservoir to push medicament stored in the reservoir into the needle and out from the needle to deliver a quantity of the medicament to the tissue region.

12. The apparatus of claim 1, further comprising a radiation delivery system operable to irradiate radiation for illuminating the tissue region.

13. The apparatus according to claim 12, wherein the radiation delivery system comprises:

a source of the radiation;

an optical fiber optically coupled with the radiation source of the radiation to receive radiation emitted by the radiation source and to deliver received radiation to at least one needle orifice.

14. The apparatus according to claim 13, wherein the optical fiber is housed inside the lumen of the needle.

15. The apparatus according to claim 13, wherein the optical fiber is mounted to an external surface region of the needle.

16. The apparatus according to claim 1, further comprising a housing configured to house the linear and rotary motion drives, the syringe system, and radiation system.

17. The apparatus according to claim 16, wherein the housing is configured to seat on or near to the tissue region.

18. A method for delivering a medicament to a region of the sclera of a subject’s eye comprising:

coupling a helical needle with a rotary motion drive of an apparatus;

rotating the needle about the motion drive rotary axis;

translating, independently from the needle rotation, the needle selectively in either proximal and distal direction along a translation axis of a linear motion drive of the apparatus relative to the subject’s eye.

19. A tissue treatment system, comprising:

an apparatus comprising:

a rotary motion drive having a motion drive rotary axis and which is configured to receive a needle and operable to rotate the needle about the motion drive rotary axis; and a linear motion drive comprising a drive screw and configured to translate the needle selectively in either proximal and distal direction along a translation axis, and further configured such that, when the apparatus is operably engaged with the tissue, the drive screw remains translationally stationary relative to the tissue during operation of the rotation motion drive to longitudinally translate the needle; and wherein the rotary motion drive and the linear motion drive are independently operatable;

at least one sensor;

at least one memory for storing data and software code instructions; and at least one processor configured to process data in accordance with the software code instructions to cause the apparatus to perform the following:

sensing, by the at least one sensor, at least one physical quantity relating to a characteristic of tissue region and a needle; and controlling, based on the sensed at least one physical quantity, the operation of the linear motion drive and/or the rotary motion drive for operably engaging the needle with the tissue region and/or a tissue irradiation parameter of a radiation source.

20. The tissue treatment system of claim 19, wherein the controlling further comprises, once the needle is operably engaged with the tissue region, controlling operation of the syringe system for the injection of a desired amount of a medicament into the tissue region.

* * * * *